US012150743B2

(12) United States Patent
Lee et al.

(10) Patent No.: US 12,150,743 B2
(45) Date of Patent: Nov. 26, 2024

(54) WEARABLE ELECTRONIC DEVICE MEASURING BLOOD PRESSURE AND METHOD FOR OPERATING THE SAME

(71) Applicant: Samsung Electronics Co., Ltd., Gyeonggi-do (KR)

(72) Inventors: Hongji Lee, Gyeonggi-do (KR); Sunok Jung, Gyeonggi-do (KR); Seongmin Je, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 407 days.

(21) Appl. No.: 17/745,930

(22) Filed: May 17, 2022

(65) Prior Publication Data

US 2022/0386885 A1    Dec. 8, 2022

Related U.S. Application Data

(63) Continuation of application No. PCT/KR2022/006338, filed on May 3, 2022.

(30) Foreign Application Priority Data

Jun. 2, 2021 (KR) .......................... 10-2021-0071334

(51) Int. Cl.
*A61B 5/021* (2006.01)
*A61B 5/00* (2006.01)
(Continued)

(52) U.S. Cl.
CPC ...... *A61B 5/02141* (2013.01); *A61B 5/02208* (2013.01); *A61B 5/02225* (2013.01);
(Continued)

(58) Field of Classification Search
CPC ............ A61B 5/02141; A61B 5/02208; A61B 5/02225; A61B 5/1116; A61B 5/681;
(Continued)

(56) References Cited

U.S. PATENT DOCUMENTS

2004/0077958 A1    4/2004   Kato et al.
2016/0143546 A1    5/2016   McCombie et al.
(Continued)

FOREIGN PATENT DOCUMENTS

JP    2006-102190 A    4/2006
JP    2020-18542 A     2/2020
(Continued)

OTHER PUBLICATIONS

Extended European Search Report dated Jun. 17, 2024.
International Search Report dated Aug. 16, 2022.

*Primary Examiner* — Jonathan T Kuo
(74) *Attorney, Agent, or Firm* — Cha & Reiter, LLC

(57) ABSTRACT

According to various embodiments, a wearable electronic device comprises a memory, a first sensor, a second sensor, and a processor, wherein the processor may be configured to, obtain a user's first biometric signal in a user's first posture through the first sensor, obtain, from an external electronic device, information about the user's first blood pressure value measured by the external electronic device in the first posture, obtain first calibration information for quantifying first blood pressure information measured in the first posture, based on information about features of the first biometric signal and the first blood pressure value, identify whether calibration data sets for a plurality of postures of the user, pre-stored in the memory, meet a specific condition for estimating second calibration information for quantifying second blood pressure information measured in the user's second posture, and when the calibration data sets meet the specific condition, estimate the second calibration information based on the calibration data sets and the first calibration information.

20 Claims, 20 Drawing Sheets

(51) Int. Cl.
*A61B 5/022* (2006.01)
*A61B 5/11* (2006.01)
*G16H 50/30* (2018.01)
*G16H 50/70* (2018.01)

(52) U.S. Cl.
CPC ............ *A61B 5/1116* (2013.01); *A61B 5/681* (2013.01); *G16H 50/30* (2018.01); *G16H 50/70* (2018.01); *A61B 2562/0219* (2013.01)

(58) Field of Classification Search
CPC .... A61B 2562/0219; A61B 2560/0223; A61B 2560/0238; A61B 5/021; A61B 5/721; A61B 5/7221; G16H 50/30
See application file for complete search history.

(56) References Cited

U.S. PATENT DOCUMENTS

| | | |
|---|---|---|
| 2017/0042433 A1 | 2/2017 | Noh et al. |
| 2017/0172431 A1* | 6/2017 | Kim ................. A61B 5/1118 |
| 2018/0263518 A1 | 9/2018 | Shimuta |
| 2018/0353089 A1 | 12/2018 | Choi et al. |
| 2019/0313916 A1 | 10/2019 | Oh et al. |
| 2019/0343407 A1 | 11/2019 | Huijbregts et al. |
| 2020/0033164 A1 | 1/2020 | Park et al. |
| 2020/0146563 A1 | 5/2020 | Lee et al. |
| 2020/0275839 A1* | 9/2020 | Park .................... A61B 5/7225 |
| 2021/0000353 A1 | 1/2021 | Fujii et al. |
| 2021/0353164 A1* | 11/2021 | Chegani ............. A61B 5/0245 |

FOREIGN PATENT DOCUMENTS

| | | |
|---|---|---|
| JP | 2020-18558 A | 2/2020 |
| KR | 10-2002-0064377 A | 8/2002 |
| KR | 10-2017-0019189 A | 2/2017 |
| KR | 10-2017-0073051 A | 6/2017 |
| KR | 10-2019-0009079 A | 1/2019 |
| KR | 10-2020-0012596 A | 2/2020 |
| KR | 10-2020-0054719 A | 5/2020 |
| KR | 10-2020-0105212 A | 9/2020 |
| WO | 2017/086071 A1 | 5/2017 |
| WO | 2020/203020 A1 | 10/2020 |

* cited by examiner

|  | f1 | f2 | f3 | f4 | f5 |
|---|---|---|---|---|---|
| Second posture | 33.27 | 66.00 | 119.61 | 1.49 | 1.29 |

| (mmHg) | Average SBP | Average DBP | Maximum SBP | Minimum SBP | Maximum DBP | Minimum DBP |
|---|---|---|---|---|---|---|
| First posture | 93.67 | 56.96 | 89.67 | 51.00 | 97.67 | 61.67 |
| Second posture | 93.59 | 61.56 | 86.00 | 55.33 | 100.67 | 67.33 |

| 2021.3.25 | SBP | DBP | f1 | f2 | f3 | f4 | f5 |
|---|---|---|---|---|---|---|---|
| second posture | 93.67 | 55.73 | 33.27 | 66.00 | 119.61 | 1.49 | 1.29 |

WEARABLE ELECTRONIC DEVICE MEASURING BLOOD PRESSURE AND METHOD FOR OPERATING THE SAME

CROSS-REFERENCE TO RELATED APPLICATION

This application is a continuation application, claiming priority under § 365(c), of an International application No. PCT/KR2022/006338, filed on May 3, 2022, which is based on and claims the benefit of a Korean patent application number 10-2021-0071334, filed on Jun. 2, 2021 in the Korean Intellectual Property Office, the disclosure of which is incorporated by reference herein in its entirety

FIELD

Various embodiments relate to a wearable electronic device measuring blood pressure and a method for operating the same.

BACKGROUND

Recently, electronic devices including a sensor capable of measuring the user's biometric information have been developed. The user may measure her body-related information using an electronic device and grasp her body conditions.

The electronic device may measure various types of biometric information, such as the user's heart rate, oxygen saturation, stress, and/or blood pressure, by means of a sensor. For example, the electronic device may sense a change in the flow of blood in the blood of the user's body portion, using a sensor. The electronic device may measure the user's various biometric information using the sensing information obtained through the sensor. For example, wearable electronic devices may continuously measure various types of biometric information about the user using sensing information obtained through a sensor in a state worn by the user.

The user who requires continuous monitoring of blood pressure in daily life may continuously measure blood pressure during activity using 24-hour ambulatory blood pressure monitoring (ABPM). However, the 24-hour ABPM may cause inconvenient to the user because the user needs to carry it with the cuff worn around the upper arm.

In everyday life, a wearable electronic device, such as a smart watch, may continuously measure the user's blood pressure while being worn by the user. In this case, the wearable electronic device may recognize the user's posture and may measure blood pressure using calibration suited for the user's posture. To this end, the wearable electronic device may request the user to update and/or add data for calibration at regular intervals. If data for calibration is not updated and/or added at regular intervals, the accuracy of the calibration suitable for the user's posture may decrease, and so may the accuracy of the measured blood pressure. In other words, since the wearable electronic device needs to obtain biometric signals for blood pressure measurement in various postures to update and/or add data for calibration at regular intervals, convenience and usability may deteriorate.

According to various embodiments of the present invention, there may be provided a method capable of increasing the accuracy of blood pressure measurement and usability by estimating data for calibration in a posture using a biometric signal measured in another posture, using data in various postures, obtained during a predetermined period when updating the data for calibration of a biometric signal (e.g., blood pressure value) according to the user's posture.

SUMMARY

According to various embodiments, a wearable electronic device may comprise a memory, a first sensor, a second sensor, and a processor. The processor may be configured to, obtain a user's first biometric signal in a user's first posture through the first sensor, obtain, from an external electronic device, information about a user's first blood pressure value measured by the external electronic device in the first posture, obtain first calibration information for quantifying first blood pressure information measured in the first posture, based on information about features of the first biometric signal and the first blood pressure value, identify whether calibration data sets for a plurality of postures of the user, pre-stored in the memory, meet a specific condition for estimating second calibration information for quantifying second blood pressure information measured in the user's second posture, and when the calibration data sets meet the specific condition, estimate the second calibration information based on the calibration data sets and the first calibration information.

According to various embodiments, a method for operating a wearable electronic device may comprise, obtaining a user's first biometric signal in a user's first posture through a first sensor included in the wearable electronic device, obtaining, from an external electronic device, information about a user's first blood pressure value measured by the external electronic device in the first posture, obtaining first calibration information for quantifying first blood pressure information measured in the first posture, based on information about features of the first biometric signal and the first blood pressure value, identifying whether calibration data sets for a plurality of postures of the user, pre-stored in the electronic device, meet a specific condition for estimating second calibration information for quantifying second blood pressure information measured in a user's second posture, and when the calibration data sets meet the specific condition, estimating the second calibration information based on the calibration data sets and the first calibration information.

According to various embodiments, an electronic device may comprise a memory, a communication module, and a processor. The processor may be configured to obtain information about a user's first biometric signal measured in a user's first posture from a wearable electronic device, through the communication module, obtain, from the external electronic device, information about the user's first blood pressure value measured by the external electronic device in the first posture, through the communication module, obtain first calibration information for quantifying first blood pressure information measured in the first posture, based on information about features of the first biometric signal and the first blood pressure value, identify whether calibration data sets for a plurality of postures of the user, pre-stored in the memory, meet a specific condition for estimating second calibration information for quantifying second blood pressure information measured in a user's second posture, and when the calibration data sets meet the specific condition, estimate the second calibration information based on the calibration data sets and the first calibration information.

DESCRIPTION OF DRAWINGS

FIGS. 6A to 6E are views illustrating a method for estimating second calibration information for a second posture using features of a first biometric signal obtained in a first posture included in calibration data sets, the blood pressure value (e.g., cuff blood pressure value) at that time, features of a second biometric signal obtained in a second posture, and the blood pressure value (e.g., cuff blood pressure value) at that time, by a wearable electronic device, according to various embodiments;

DETAILED DESCRIPTION

According to various embodiments, there may be provided a method and apparatus capable estimating calibration data in a posture. The calibration data may be measured using a biometric signal measured in another posture and data in various postures that is obtained during a predetermined updating period.

According to various embodiments, a wearable electronic device may estimate data for calibration in a posture using a biometric signal measured in another posture, using data in various postures, obtained during a predetermined period when updating the data for calibration of a biometric signal (e.g., blood pressure value) according to the user's posture, thereby increasing the accuracy of blood pressure measurement and usability.

A user can have their blood pressure continuously measured by an electronic device that is worn on their person, such as a smartwatch, among others.

Figure 1:
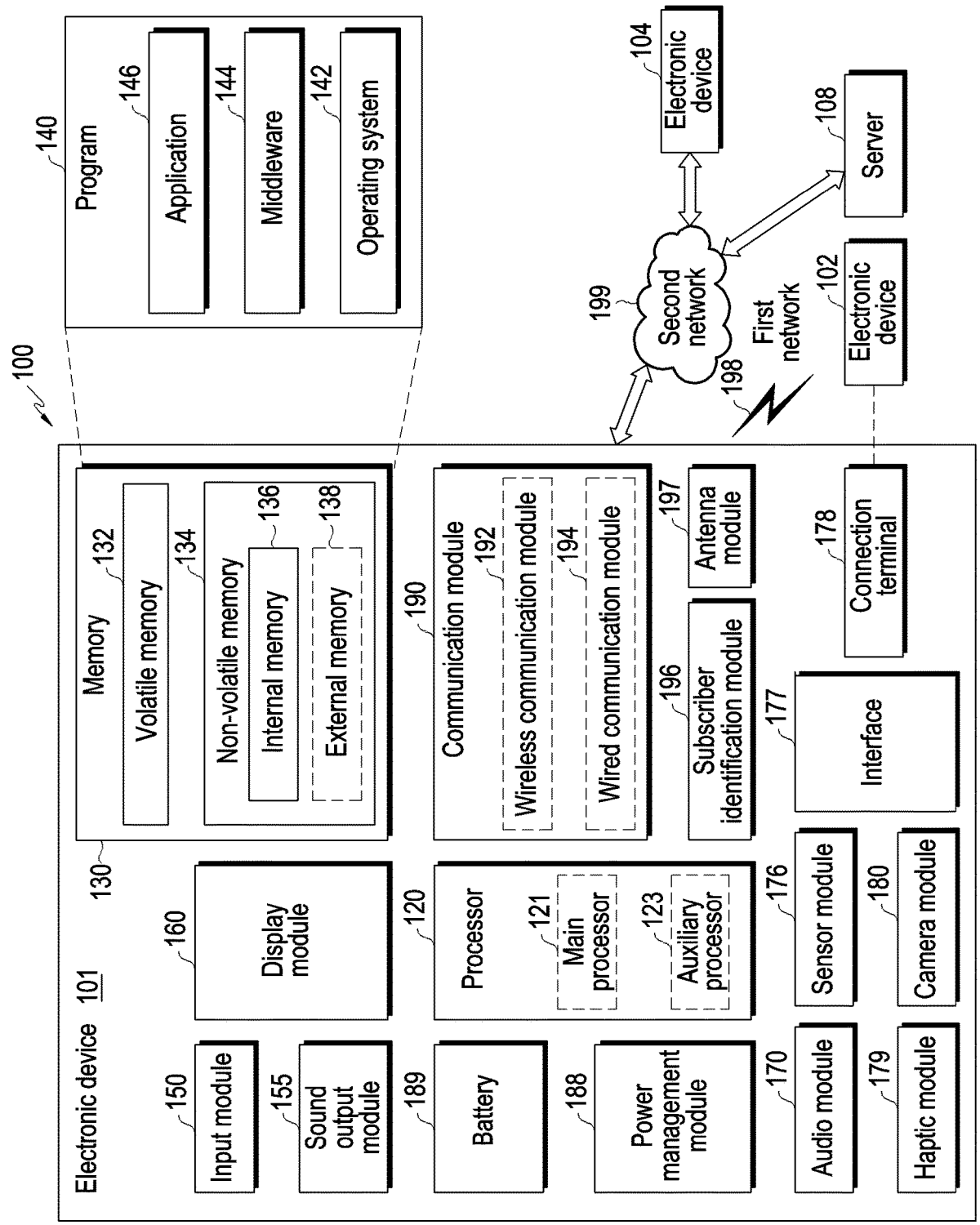
FIG. 1 is a block diagram illustrating an electronic device in a network environment according to various embodiments.

FIG. 1 is a block diagram illustrating an electronic device 101 in a network environment 100 according to various embodiments. Referring to FIG. 1, the electronic device 101 in the network environment 100 may communicate with at least one of an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one (e.g., the connecting terminal 178) of the components may be omitted from the electronic device 101, or one or more other components may be added in the electronic device 101. According to an embodiment, some (e.g., the sensor module 176, the camera module 180, or the antenna module 197) of the components may be integrated into a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be configured to use lower power than the main processor 121 or to be specified for a designated function. The auxiliary processor 123 may be implemented as separate from, or as part of the main processor 121.

The term "processor" shall be understood to refer to both the singular and plural contexts in this document.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. The artificial intelligence model may be generated via machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by other component (e.g., the processor 120) of the electronic device 101, from the outside (e.g., a user) of the electronic device 101. The input module 150 may include, for example, a microphone, a mouse, a keyboard, keys (e.g., buttons), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display 160 may include, for example, a display, a hologram device, or a projector and control circuitry to control a corresponding one of the display, hologram device, and projector. According to an embodiment, the display 160 may include a touch sensor configured to detect a touch, or a pressure sensor configured to measure the intensity of a force generated by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or motion) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device 104 via a first network 198 (e.g., a short-range communication network, such as Bluetooth™, wireless-fidelity (Wi-Fi) direct, or infrared data association (IrDA)) or a second network 199 (e.g., a long-range communication network, such as a legacy cellular network, a 5G network, a next-generation communication network, the Internet, or a computer network (e.g., local area network (LAN) or wide area network (WAN)). These various types of communication modules may be implemented as a single component (e.g., a single chip), or may be implemented as multi components (e.g., multi chips) separate from each other. The wireless communication module 192 may identify or authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna.

The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device). According to an embodiment, the antenna module 197 may include one antenna including a radiator formed of a conductor or conductive pattern formed on a substrate (e.g., a printed circuit board (PCB)). According to an embodiment, the antenna module 197 may include a plurality of antennas (e.g., an antenna array). In this case, at least one antenna appropriate for a communication scheme used in a communication network, such as the first network 198 or the second network 199, may be selected from the plurality of antennas by, e.g., the communication module 190. The signal or the power may then be transmitted or received between the communication module 190 and the external electronic device via the selected at least one antenna. According to an embodiment, other parts (e.g., radio frequency integrated circuit (RFIC)) than the radiator may be further formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. The external electronic devices 102 or 104 each may be a device of the same or a different type from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or health-care) based on 5G communication technology or IoT-related technology.

The electronic device according to various embodiments of the disclosure may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. Some of the plurality of entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

The electronic device 101 can measure the user's blood pressure (and other biometric data) using sensor modules 176. In particular, a wearable electronic device 101, such as a smartwatch can continuously measure the user's blood pressure.

However, a user's blood pressure can vary based on their posture. Typically, the baseline blood pressure is to be taken in the seated position. If the user is standing, the measured blood pressure changes are result of the user's posture. Nevertheless, the measured blood pressure of the user when standing or in another position can be adjusted with calibration information associated with the user's posture.

Calibration information is associated with a posture, and can be used to adjust a blood pressure reading of a user in the position, to make the reading comparable to, for example, a blood pressure reading in the seated position. Accordingly, the memory 132 can store calibration information for various common user postures. The sensor module 176 can measure the user's blood pressure FIG. 2 is a block diagram illustrating a schematic configuration of a wearable electronic device according to various embodiments.

Figure 2:
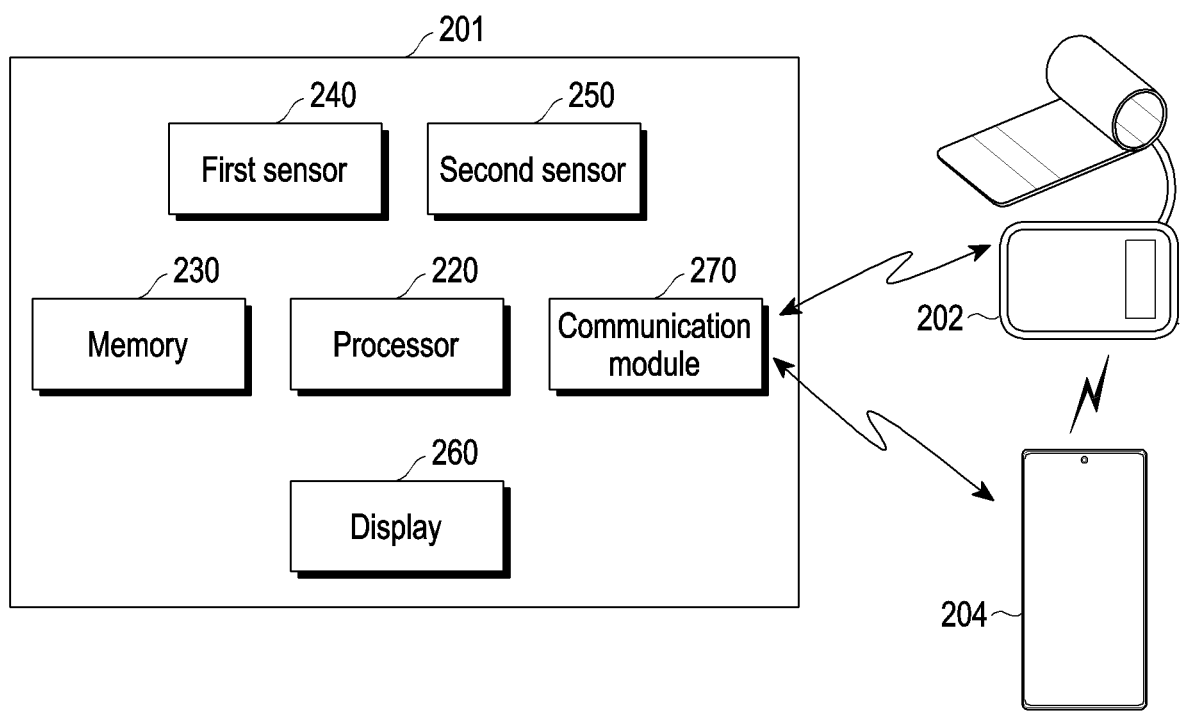
FIG. 2 is a block diagram illustrating a schematic configuration of a wearable electronic device according to various embodiments.

Referring to FIG. 2, a wearable electronic device 201 (e.g., the electronic device 101 of FIG. 1) may include a processor 220, a memory 230, a first sensor 240, a second sensor 250, a display 260, and/or a communication module 270. For example, the wearable electronic device 201 may be implemented in a form wearable on the user, such as a smart watch, a smart band, a smart ring, a wireless earphone, or smart glasses.

According to various embodiments, the processor 220 (e.g., the processor 120 of FIG. 1) may control the overall operation of the wearable electronic device 201.

According to various embodiments, the processor 220 may obtain the user's biometric signal through the first sensor 240. The processor 220 may obtain or measure the user's blood pressure value based on the biometric signal. The processor 220 may display information about the user's blood pressure value on the display 260 (e.g., the display module 160 of FIG. 1). For example, the first sensor 240 (e.g., the sensor module 176 of FIG. 1) may include a Photoplethysmogram (PPG) sensor, and the biometric signal may include a PPG signal. For example, the first sensor 240 may radiate an optical signal to the user's body portion (e.g., a blood vessel positioned on a finger or wrist or a radial artery below the wrist) using a plurality of light emitting elements capable of emitting different wavelengths of light, accumulate the optical charge corresponding to the amount of the light reflected through, or transmitted through a plurality of light receiving elements, and convert the biometric signal, in analog current form according to the accumulated optical charge into a digital signal. As another example, the first sensor 240 may include a plurality of electrodes. The electrode may be in direct contact with the user's skin and may be used to sense or detect the voltage corresponding to the electrical resistance or the voltage corresponding to electrical conductance. The electrode may measure an analog biometric signal (e.g., BIA signal or ECG signal) and convert the measured analog signal into a digital signal. The first sensor 240 may operate to obtain at least two or more biometric information among a plurality of biometric information, e.g., heart rate, blood oxygen saturation, BIA signal, ECG signal, and blood pressure. For example, the sensor module may operate such that the heart rate, blood oxygen saturation, and BIA signal are simultaneously obtained. According to an embodiment, the first sensor 240 may include a laser diode (LD) and an image sensor.

According to various embodiments, the processor 220 may identify the user's posture through the second sensor 250 (e.g., the sensor module 176 of FIG. 1). For example, the processor 220 may measure, through the second sensor 250, the signal corresponding to a movement of the user wearing the wearable electronic device 201 when a biometric signal is obtained through the first sensor 240 and may identify the user's posture based on the signal corresponding to the movement. For example, the second sensor 250 may include at least one of a motion sensor, a gyro sensor, an acceleration sensor, a gravity sensor (or a geomagnetic sensor), or a barometer sensor. Without being limited thereto, the second sensor 250 may include various types of sensors capable of detecting the posture (or movement) of the user wearing the wearable electronic device 201. According to an embodiment, the processor 220 may identify the user's posture based on identifying the air pressure (e.g., air pressure gradient and air pressure peak-to-peak (P2P) value) of the air pressure sensor according to a change in the displacement of the wearable electronic device 201 and/or acceleration information (e.g., the size on the three axes (e.g., x, y, and z axes) from the acceleration sensor. According to various embodiments, the processor 220 may identify the user's posture based on a combination of the data obtained from the first sensor 240 and/or the second sensor 250.

According to various embodiments, the processor 220 may identify the user's posture when measuring blood pressure through the second sensor 250 and adjust the blood pressure value using pre-stored calibration information based on the user's posture. That is, the pre-stored calibration information can include calibration information corresponding to a number of possible user postures. The processor 220 can select the calibration data associated with the identified user's posture, and adjust the measured blood pressure with the first sensor 240 with the calibration data that is associated with the identified user's posture.

The blood pressure value measured by analyzing the biometric signal may differ from the actual blood pressure value according to the user's posture. The processor 220 may store, in the memory 230 (e.g., the memory 130 of FIG. 1), calibration data sets measured in various postures (e.g., the first posture—for example, sitting on a chair, or the second posture—for example, standing, other examples, may include lying down, sitting on the floor) using the first sensor 240 and an external blood pressure monitor 202. For example, the processor 220 may identify calibration information about the identified user posture among the calibration data sets stored in the memory 230 (e.g., the memory 130 of FIG. 1) and measure the blood pressure value using the identified calibration information. The processor 220 may display information about the user's calibrated blood pressure value on the display 260. Thus, the processor 220 may more precisely measure the blood pressure value by performing calibration suitable for the user's posture when continuously measuring the user's blood pressure.

According to various embodiments, the processor 220 may obtain calibration data sets based on the features of the biometric signal (the blood pressure signal as measured by the first sensor 240) and the blood pressure values (e.g., the cuff blood pressure value measured through a cuff blood pressure monitor) according to the user's posture. For example, the calibration data set may include the features of the biometric signal obtained in the first posture at a designated time, the blood pressure value (e.g., cuff blood pressure value) at that time, features of the biometric signal obtained in the second posture, and the blood pressure value (e.g., cuff blood pressure value) at that time.

For example, the features of the biometric signal may be measured through the first sensor 240, and the cuff blood pressure value may be measured by the external blood pressure monitor 202 (e.g., cuff blood pressure monitor) at proximate times, when the user is in the same posture. In other words, each of the calibration data sets may include information about the feature and blood pressure value (e.g., cuff blood pressure value) of the biometric signal obtained from each of the plurality of user postures at different times. For example, the calibration data sets may be obtained from an external electronic device 204 or generated by the wearable electronic device 201. For example, the processor 220 may receive calibration data sets through the external electronic device 204 operatively connected with the electronic device. As another example, the processor 220 may receive pre-stored calibration data sets through a server connected on the same account.

The features can include, among other things, the peak level of waveform of a PPG signal, the time corresponding to each peak, the area of a PPG waveform, the ratio between features, and/or a combination thereof. According to various embodiments, the processor 220 may store a user's personal information (e.g., gender, age, height, weight, or information about the medicine the user is taking). For example, the processor 220 may measure the blood pressure value based on the user's personal information. According to an embodiment, if it is identified that a change in the user's personal information (e.g., weight or information about the medicine taken) stored in the memory 230 is a predetermined level or more, the processor 220 may guide the user to update the calibration data.

According to various embodiments, the processor 220 may store the calibration data sets in the memory 230. The processor 220 may periodically update the data included in the calibration data sets. For example, the processor 220 may obtain the blood pressure value (e.g., cuff blood pressure value) from the external blood pressure monitor 202 while obtaining the biometric signal through the first sensor 240 in the user's first posture (e.g., lying posture) at a first time (e.g., the date the calibration data is measured).

Further, the processor 220 may obtain the biometric signal through the first sensor 240 in the user's second posture (e.g., sitting or standing posture) at the first time and obtain the blood pressure value (e.g., cuff blood pressure value) from the external blood pressure monitor 202. The processor 220 may store the features of the biometric signal obtained in the first posture and blood pressure value (e.g., cuff blood pressure value) and the features of the biometric signal obtained in the second posture and blood pressure value (e.g., cuff blood pressure value), as a first calibration data set at the first time. For example, the processor 220 may obtain and store the first calibration data set, provided that the biometric signals and blood pressure values in the first and second posture are taken within a designated time (e.g., within a maximum of 10 minutes). For example, after the operation of obtaining the first calibration data set starts, the processor 220 may complete the acquisition and storage of the features of the biometric signal and blood pressure value (e.g., cuff blood pressure value) from each of the first posture and the second posture within the designated time. For example, after the operation of obtaining the first calibration data set starts, if the processor 220 fails to obtain the features of the biometric signal and blood pressure value (e.g., cuff blood pressure value) from each of the first posture and the second posture within the designated time, the processor 220 may display a message guiding the user to re-measure.

According to the same method, the processor 220 may store the second calibration data set at the second time different from the first time. For example, the processor 220 may obtain a blood pressure value from the external blood pressure monitor 202 while obtaining a biometric signal through the first sensor 240 in the user's first posture (e.g., lying posture) at the second time. The processor 220 may obtain the blood pressure value from the external blood pressure monitor 202 while obtaining the biometric signal through the first sensor 240 in the user's second posture (e.g., sitting or standing posture) at the second time. The processor 220 may store the features of the biometric signal obtained in the first posture and blood pressure value and the features of the biometric signal obtained in the second posture and blood pressure value, as a second calibration data set at the second time. For example, there may be a certain time interval between the first time and the second time. For example, the time interval may be a time interval of at least 10 minutes or more. For example, if the time interval between the first time and the second time is shorter than a designated time interval (e.g., 10 minutes), the processor 220 may determine that the features and blood pressure values (e.g., cuff blood pressure values) of the biometric signal measured at the first time and the second time are measured at the same time.

According to an embodiment, the processor 220 may periodically delete the data included in the calibration data sets. For example, the processor 220 may delete the calibration data sets stored in the memory for a certain period (e.g., 3 months or 6 months) or longer. For example, when the number of pre-stored calibration data sets is larger than or equal to a designated number, the processor 220 may delete the calibration data sets, sequentially from the first stored calibration data set.

However, since the biometric signal needs to be measured in a plurality of postures, every specific time for the wearable electronic device 201 to secure calibration data sets by the above-described method, usability may deteriorate. Thus, the processor 220 may estimate the features and blood pressure value of the biometric signal, obtainable in the second posture, based on the plurality of calibration data sets stored in the memory 230 and the features and blood pressure value (e.g., cuff blood pressure value) of the biometric signal obtained in the first posture.

According to various embodiments, the processor 220 may obtain the user's first biometric signal through the first sensor 240 and features of the first biometric signal, in the user's first posture at a specific time. The processor 220 may receive information about a first blood pressure value measured in the first posture at the specific time by the external blood pressure monitor 202, from the external blood pressure monitor 202 through the communication module 270 (e.g., the communication module 190 of FIG. 1). The processor 220 may receive, through the user's input, information about the first blood pressure value measured in the first posture at the specific time by the external blood pressure monitor 202.

According to various embodiments, the processor 220 may obtain first calibration information about the user's first posture at the specific time, based on the features of the first biometric signal and the first blood pressure value. For example, the first calibration information may include information about the specific time, first posture (e.g., lying posture), first blood pressure value (e.g., cuff systolic blood pressure (SBP) and/or cuff diastolic blood pressure (DBP)) and the features of the first biometric signal (e.g., the peak value of the waveform of the PPG signal, the time corresponding to each peak, the area of the PPG waveform, and/or the ratio between features).

According to various embodiments, the processor 220 may obtain second calibration information about the second posture at the specific time, based on the features of the first biometric signal and calibration data sets for the plurality of user postures pre-stored in the memory 230. For example, the second calibration information may include information about the features and blood pressure values (e.g., cuff blood pressure values) of the biometric signals measurable in the user's second posture at the specific time. For example, the second calibration information may include information about the specific time, second posture (e.g., sitting or standing posture), second blood pressure value (e.g., cuff systolic blood pressure (SBP) and/or cuff diastolic blood pressure (DBP)) and the features of the second biometric signal (e.g., the peak value of the waveform of the PPG signal, the time corresponding to each peak, the area of the PPG waveform, and/or the ratio between features). In other words, the processor 220 may estimate and obtain second calibration information about the second posture based on the calibration data sets for the plurality of user postures pre-stored in the memory 230 and the first calibration information, rather than directly measuring the biometric signal and blood pressure value (e.g., cuff blood pressure value) from the user.

According to various embodiments, the processor 220 may store the first calibration information and the second calibration information, as a first calibration data set, in the memory 230. For example, the processor 220 may add the first calibration data set to the plurality of pre-stored calibration data sets.

According to various embodiments, the external blood pressure monitor 202 may measure the user's blood pressure value (e.g., cuff blood pressure value). For example, the external blood pressure monitor 202 may include a cuff blood pressure monitor. For example, the external blood pressure monitor 202 may measure the user's blood pressure in a manner different from the manner in which the wearable electronic device measures the user's blood pressure. For example, the external blood pressure monitor 202 may measure the user's blood pressure value according to an oscillometric method and/or a korotkoff sounds method. The external blood pressure monitor 202 may transmit the measured blood pressure value to the wearable electronic device 201 and/or the electronic device 204.

According to various embodiments, the electronic device 204 may estimate the features and blood pressure value of the biometric signal, obtainable in the second posture, based on the plurality of calibration data sets and the features and blood pressure value (e.g., cuff blood pressure value) of the biometric signal obtained in the first posture. For example, the electronic device 204 may store a plurality of calibration data sets in a memory (not shown) (e.g., the memory 130 of FIG. 1) of the electronic device 204. The electronic device 204 may receive information about the biometric signal obtained in the first posture from the wearable electronic device 201 through the communication module (e.g., the communication module 190 of FIG. 1) and may receive information about the blood pressure value obtained in the first posture from the external blood pressure monitor 202. The electronic device 204 may obtain the first calibration information according to the above-described method and estimate and obtain the second calibration information based on the first calibration information. Further, the electronic device 204 may store the first calibration data set in a memory (not shown) based on the first calibration information and the second calibration information. The electronic device 204 may transmit information about the first calibration data set to the wearable electronic device 204.

Meanwhile, at least some of the operations performed by the wearable electronic device 201, described below, may be performed by the processor 220.

Figure 3:
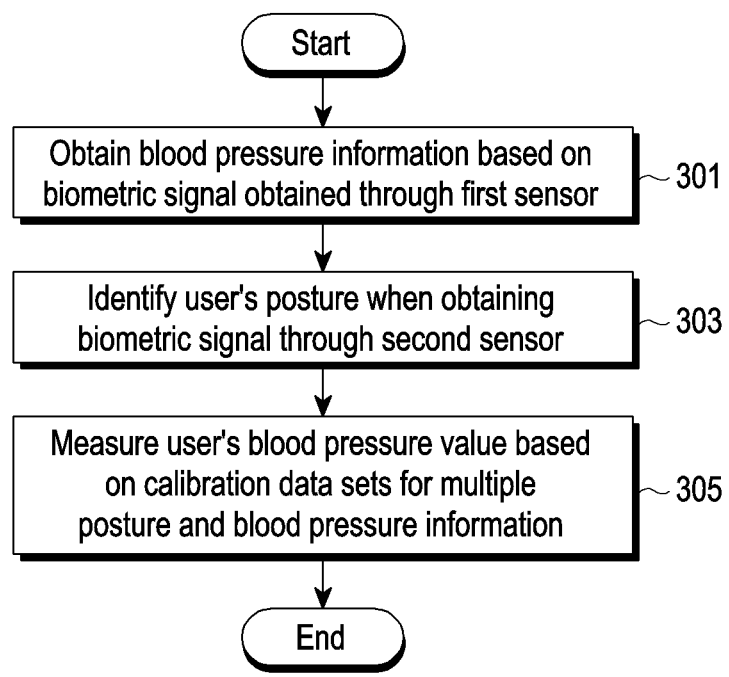
FIG. 3 is a flowchart illustrating a method for measuring the blood pressure using calibration according to the user's posture, by a wearable electronic device, according to various embodiments.

FIG. 3 is a flowchart illustrating a method for measuring the blood pressure using calibration according to the user's posture, by a wearable electronic device, according to various embodiments.

Referring to FIG. 3, according to various embodiments, in operation 301, the wearable electronic device 201 may obtain the user's blood pressure information based on the biometric signal obtained through the first sensor 240. For example, the wearable electronic device 201 may obtain blood pressure information by analyzing the user's biometric signal.

According to various embodiments, in operation 303, the wearable electronic device 201 may identify the user's posture when obtaining a biometric signal through the second sensor 250.

According to various embodiments, in operation 305, the wearable electronic device 201 may obtain the user's blood pressure value based on blood pressure information and calibration data sets for a plurality of postures of the user stored in the memory 230. For example, the wearable electronic device 201 may identify the calibration data set matching the features and blood pressure value of the biometric signal and the user's posture from among the calibration data sets for the plurality of postures to thereby calibrate the blood pressure information and measure the user's blood pressure value based on the calibrated blood pressure information. The wearable electronic device 201 may store the calibration data and the quantified blood pressure value in the memory 230 or display it on the display 260.

Figure 4A:
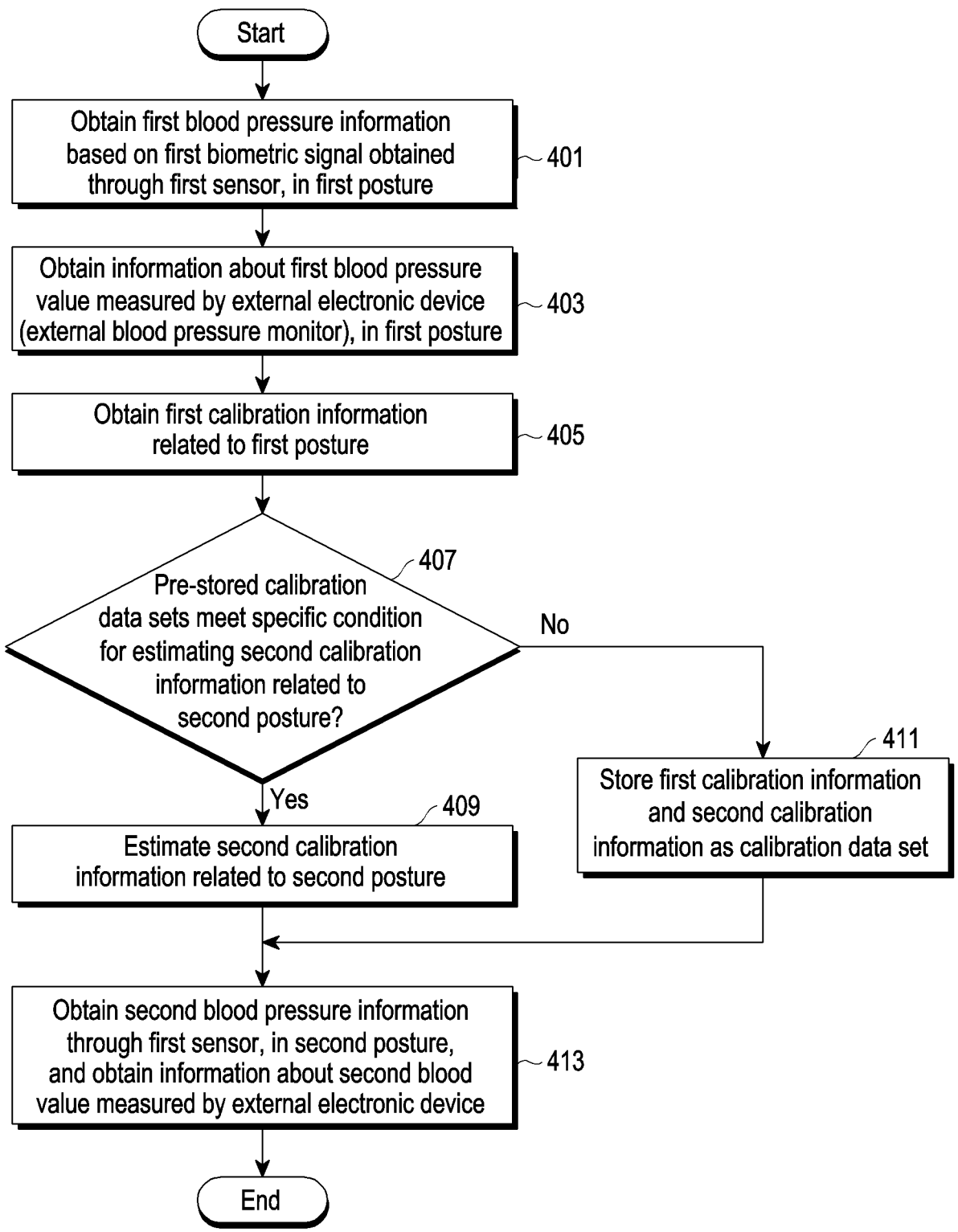
FIGS. 4A and 4B are a flowchart and a view illustrating a method for obtaining calibration data used to measure the blood pressure by a wearable electronic device, according to various embodiments.
Figure 4B:
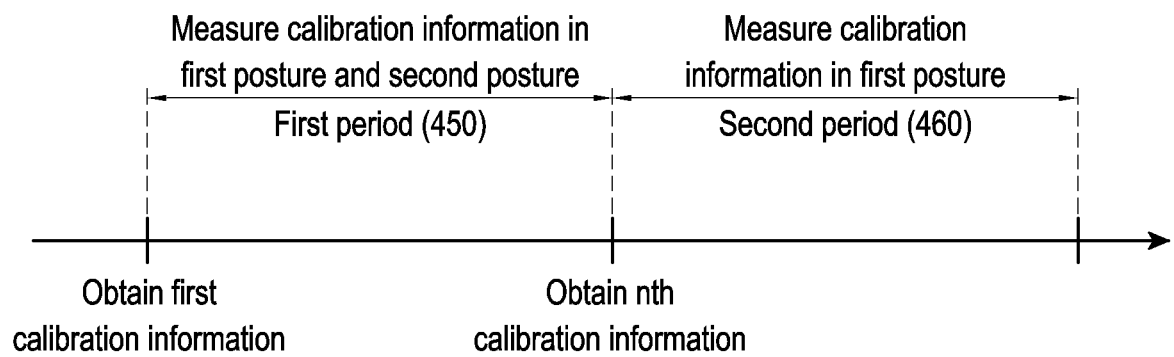

FIGS. 4A and 4B are a flowchart and a view illustrating a method for obtaining calibration data used to measure the blood pressure by a wearable electronic device, according to various embodiments.

Referring to FIG. 4A, according to various embodiments, in operation 401, the wearable electronic device 201 may directly obtain the user's first biometric signal through the first sensor 240 in the user's first posture (e.g., lying posture).

According to various embodiments, in operation 403, the wearable electronic device 201 may obtain information about the first blood pressure value measured by an external electronic device (e.g., the external blood pressure monitor 202) in the first posture from the external electronic device 202. The first blood pressure value may mean a cuff blood pressure value measured by the external electronic device 202 (e.g., cuff blood pressure monitor). According to an embodiment, operations 401 and 403 may be performed simultaneously.

According to various embodiments, in operation 405, the wearable electronic device 201 may obtain first calibration information related to the first posture. For example, the first calibration information may refer to information for quantifying the user's first blood pressure information (e.g., information for measuring blood pressure in the user's first biometric signal) measured in the first posture. For example, the first calibration information may include the features of the user's first biometric signal measured through the first sensor 240 in the first posture and information about the user's first blood pressure value (e.g., cuff blood pressure value) measured by the external electronic device 202 in the first posture.

According to various embodiments, in operation 407, the wearable electronic device 201 may identify whether the calibration data sets for the plurality of postures of the user pre-stored in the memory 230 meet a specific condition for estimating the second calibration information related to the second posture. For example, the specific condition may mean a condition as to whether the calibration data sets include sufficient data to estimate the second calibration information related to the second posture (e.g., sifting or standing posture) different from the first posture. For example, the specific condition may be met if the calibration data sets include a specific number of, or more, data or include the same or similar data to the features and first blood pressure value of the first biometric signal included in the first calibration information.

According to various embodiments, when the calibration data sets meet the specific condition (Yes in operation 407), the wearable electronic device 201 may estimate the second calibration information related to the second posture in operation 409. For example, the second calibration information may refer to information for quantifying the user's second blood pressure information (e.g., information for measuring blood pressure in the user's first biometric signal) measured in the second posture. For example, the wearable electronic device 201 may obtain the second calibration information related to the user's second posture based on the first calibration information and the pre-stored calibration data sets. The wearable electronic device 201 does not obtain information about the second blood pressure value measured in the second posture from the external electronic device (e.g., the external blood pressure monitor 202) or directly measure the user's biometric signal, but may estimate and obtain the second calibration information related to the second posture.

According to various embodiments, when the calibration data sets do not meet the designated condition (No in operation 407), in operation 411, the wearable electronic device 201 may obtain the second blood pressure information based on the second biometric signal obtained through the first sensor 240 directly from the user in the second posture and obtain information about the second blood pressure value measured by the external electronic device (e.g., the external blood pressure monitor 202). The second blood pressure value may mean a cuff blood pressure value measured by the external electronic device 202 (e.g., cuff blood pressure monitor). For example, the wearable electronic device 202 may obtain the second calibration information based on information about the features and second blood pressure value of the second biometric signal obtained by directly measuring the user's biometric signal in the second posture.

According to various embodiments, in operation 413, the wearable electronic device 201 may store the first calibration information and the second calibration information, as a calibration data set. Thereafter, when measuring the user's blood pressure value, the wearable electronic device 201 may perform the operation of measuring the blood pressure value according to the user's posture using the stored calibration data set (e.g., the calibration data set including the estimated second calibration information).

Meanwhile, although it is described herein that data for calibration is obtained in two postures, and calibration is performed based thereupon for ease of convenience, the technical spirit of the present invention is not limited thereto. For example, the wearable electronic device 201 may obtain data for calibration in a plurality of postures (e.g., three or more postures) and, based thereupon, perform calibration for a plurality of postures (e.g., three or more postures).

Referring to FIG. 4B, the wearable electronic device 201 may obtain calibration information or calibration data through the first sensor 240. For example, the wearable electronic device 201 may sense the user's biometric signal to obtain calibration information in at least one of the first posture and the second posture through the first sensor 240.

According to various embodiments, in a first period 450, the wearable electronic device 201 may obtain the user's biometric signal to obtain calibration information in both the first posture and the second posture. For example, the first section 450 may mean a period during which the number of calibration data sets stored in the memory 230 is not sufficiently accumulated. For example, the first period 450 may be a period during which the number of calibration data sets stored in the memory 230 is less than a specific number (e.g., n, where n is a natural number). In the first period 460, the wearable electronic device 201 may provide a guide to the user to obtain a biometric signal in both the first posture and the second posture.

According to various embodiments, in a second period 460, the wearable electronic device 201 may obtain the user's biometric signal to obtain calibration information only in either the first posture or the second posture. For example, the second period 460 may be a period during which the number of calibration data sets stored in the memory 230 is a designated number or more. For example, the designated number may mean a number sufficient to estimate calibration information related to the other one (e.g., the second posture) of the first and second postures. For example, the designated number may be set automatically by the processor 220 or by the user. For example, the designated number may be five.

According to various embodiments, in the second period 460, if the calibration data sets stored in the memory 230 do not include a data set matching the biometric signal obtained in any one posture (e.g., the first posture) of the first posture and the second posture, the wearable electronic device 201 may not estimate the calibration information related to the other posture (e.g., the second posture) of the first posture and the second posture. In the second period 460, the wearable electronic device 201 may provide a guide to the user to obtain a biometric signal in the second posture.

Figure 5:
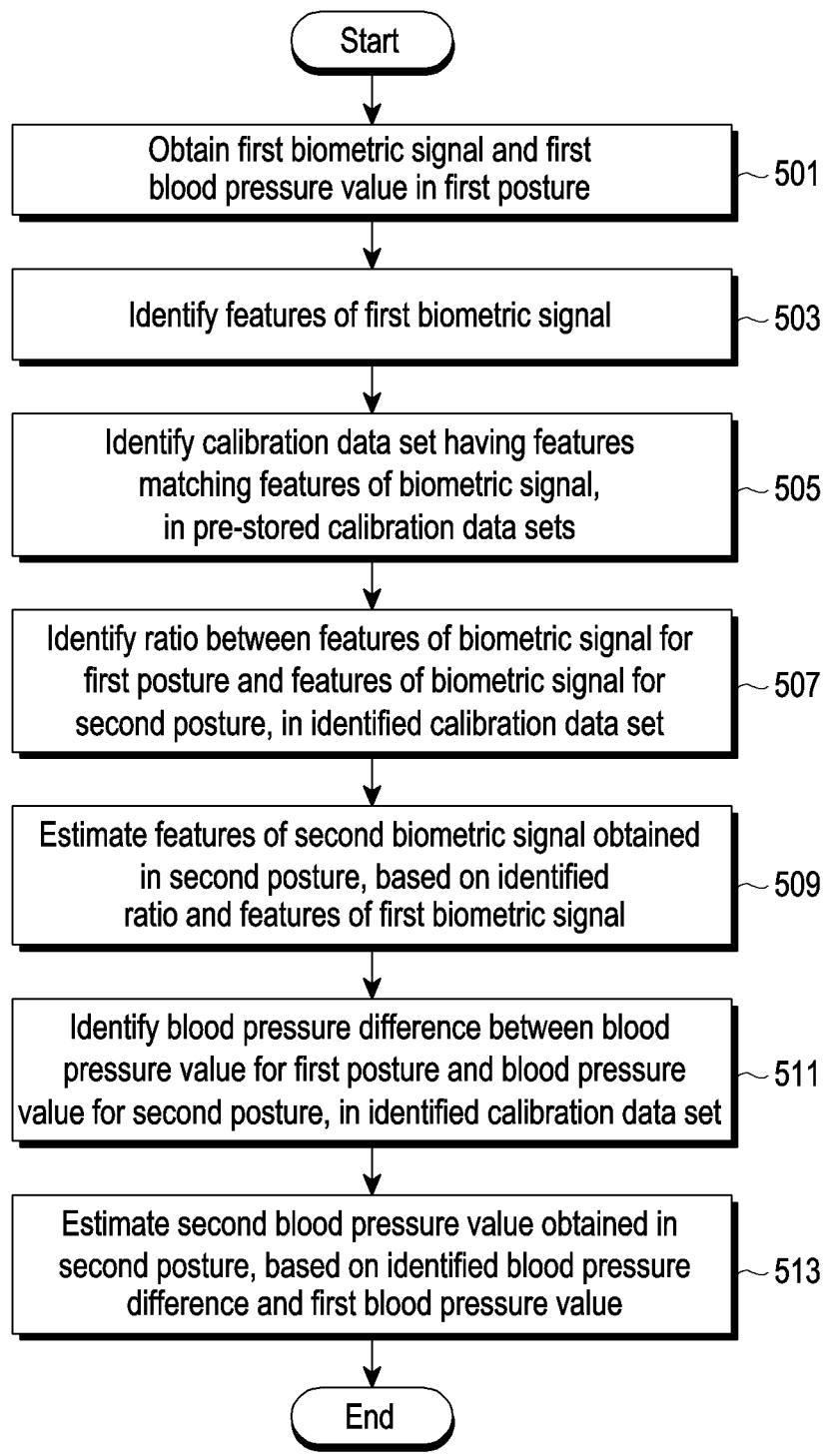
FIG. 5 is a flowchart illustrating a method for estimating second calibration information for a second posture using features of a first biometric signal obtained in a first posture included in calibration data sets, the blood pressure value (e.g., cuff blood pressure value) at that time, features of a second biometric signal obtained in a second posture, and the blood pressure value (e.g., cuff blood pressure value) at that time, by a wearable electronic device, according to various embodiments.

FIG. 5 is a flowchart illustrating a method for estimating second calibration information for a second posture using features of a first biometric signal obtained in a first posture included in calibration data sets, the blood pressure value (e.g., cuff blood pressure value) at that time, features of a second biometric signal obtained in a second posture, and the blood pressure value (e.g., cuff blood pressure value) at that time, by a wearable electronic device, according to various embodiments.

Referring to FIG. 5, according to various embodiments, in operation 501, the wearable electronic device 201 may obtain a first biometric signal and a first blood pressure value in a first posture. For example, the wearable electronic device 201 may obtain the first biometric signal through the first sensor 240 and may obtain the first blood pressure value (e.g., cuff blood pressure value) measured by the external blood pressure monitor 202 through the communication module 270 or the user input.

According to various embodiments, in operation 503, the wearable electronic device 201 may identify the features of the first biometric signal (e.g., PPG signal). For example, the features of the first biometric signal may include the peak level of waveform of the PPG signal, the time corresponding to each peak, the area of the PPG waveform, the ratio between features, and/or a combination thereof. For example, each of the features of the first biometric signal may include a value for the feature.

According to various embodiments, in operation 505, the wearable electronic device 201 may identify a calibration data set obtained at a specific time, which has features matching the features of the first biometric signal among pre-stored calibration data sets. For example, the calibration data set may include first calibration information about the first posture and second calibration information about the second posture. The wearable electronic device may identify the calibration data set including calibration information having features similar to the features matching the features of the first biometric signal in the calibration information about the first posture of each of the pre-stored calibration data sets.

According to various embodiments, in operation 507, the wearable electronic device 201 may identify the ratio between the features (e.g., the values of the features) of the biometric signal for the first posture and the features (e.g., the values of the features) of the biometric signal for the second posture in the identified calibration data set obtained at the specific time.

According to various embodiments, in operation 509, the wearable electronic device 201 may estimate the features of the second biometric signal that may be obtained in the second posture, based on the features of the first biometric signal and the identified ratio. For example, the wearable electronic device 201 may estimate the respective values of the features of the second biometric signal that may be obtained in the second posture, by applying the identified ratio to the respective values of the features of the first biometric signal (e.g., multiplying the respective values of the features of the first biometric signal by the identified ratio).

According to various embodiments, in operation 511, the wearable electronic device 201 may identify a blood pressure difference between the blood pressure value (e.g., cuff blood pressure value) for the first posture and the blood pressure value (e.g., cuff blood pressure value) for the second posture, measured at the specific time, in the identified calibration data set. For example, the wearable electronic device 201 may identify a first blood pressure difference between the systolic blood pressure (SBP) for the first posture and the systolic blood pressure (SBP) for the second posture, measured at the specific time and identify a second blood pressure difference between the diastolic blood pressure (DBP) for the first posture and the diastolic blood pressure (DBP) for the second posture, measured at the specific time.

According to various embodiments, in operation 513, the second blood pressure value obtained in the second posture may be estimated based on the identified blood pressure difference and the first blood pressure value. For example, the wearable electronic device 201 may estimate the second blood pressure value by applying the identified blood pressure difference to the first blood pressure value (e.g., adding or subtracting the identified blood pressure difference to/from the first blood pressure value). For example, the wearable electronic device 201 may identify the systolic blood pressure of the second blood pressure value by adding the first blood pressure difference to the systolic blood pressure included in the first blood pressure value and identify the diastolic blood pressure of the second blood pressure value by adding the second blood pressure difference to the diastolic blood pressure included in the first blood pressure value.

FIGS. 6A to 6E are views illustrating a method for estimating second calibration information for a second posture using features of a first biometric signal obtained in a first posture included in calibration data sets, the blood pressure value (e.g., cuff blood pressure value) at that time, features of a second biometric signal obtained in a second posture, and the blood pressure value (e.g., cuff blood pressure value) at that time, by a wearable electronic device, according to various embodiments.

Figure 6A:
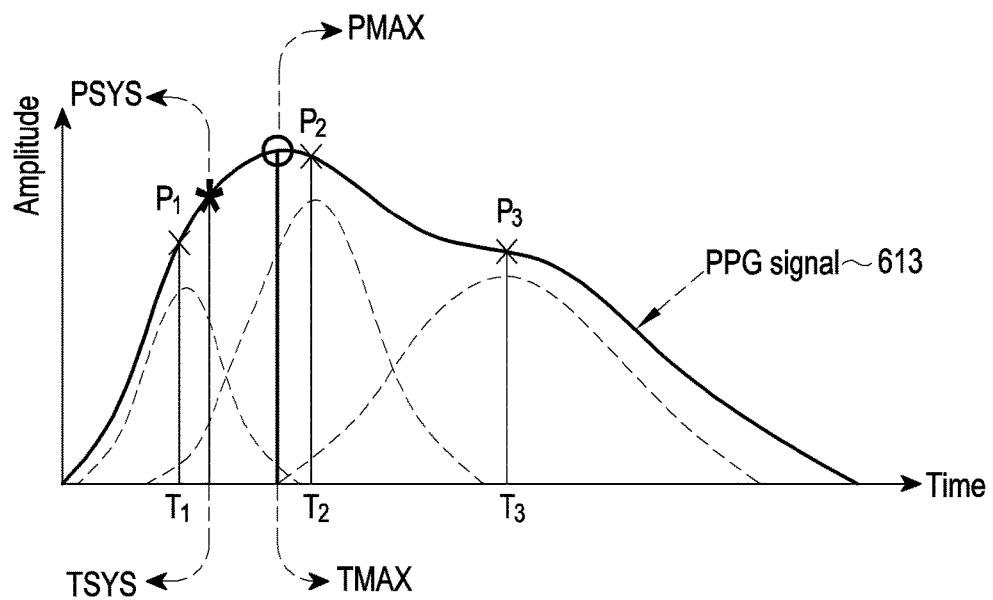

Referring to FIG. 6A, the wearable electronic device 201 may obtain first calibration information 610 for the first posture. The first calibration information 610 may include information about a specific time (e.g., Mar. 25, 2021), information about a first posture (e.g., lying posture), information 612 about a first blood pressure value (systolic and diastolic), and information 615 about features of a first biometric signal 613. In certain embodiments, the features of the first biometric signal 163 can included Fourier transform coefficients.

According to various embodiments, the wearable electronic device 201 may obtain the information 612 about the first blood pressure value measured by an external blood pressure monitor 202 at the specific time. For example, the information about the first blood pressure value may include information about a systolic blood pressure Cal_SBP and a diastolic blood pressure Cal_DBP measured in the first posture.

According to various embodiments, the wearable electronic device 201 may obtain a first biometric signal 613 (e.g., a PPG signal) through the first sensor 240 and identify the features of the first biometric signal 613. The wearable electronic device 201 may obtain information 615 about the features of the first biometric signal 613. For example, a first feature f1, a second feature f2, a third feature f3, a fourth feature f4, and a fifth feature f5 may be values generated by peak levels (e.g., P1, P2, and P3) of the waveform of the first biometric signal 613 (e.g., PPG signal), the times (e.g., T1, T2, and T3) corresponding to the peaks, the amplitude PMAX and time TMAX at the maximum value point in the systolic period of the PPG signal, the amplitude PSYS and time TSYS at a specific point in the systolic period, the area of the waveform, the ratio between features, and/or a combination thereof. However, the values indicating the features of the first biometric signal 613 and the number thereof are merely for convenience of description, and the technical spirit of the present invention may not be limited thereto.

Figure 6B:
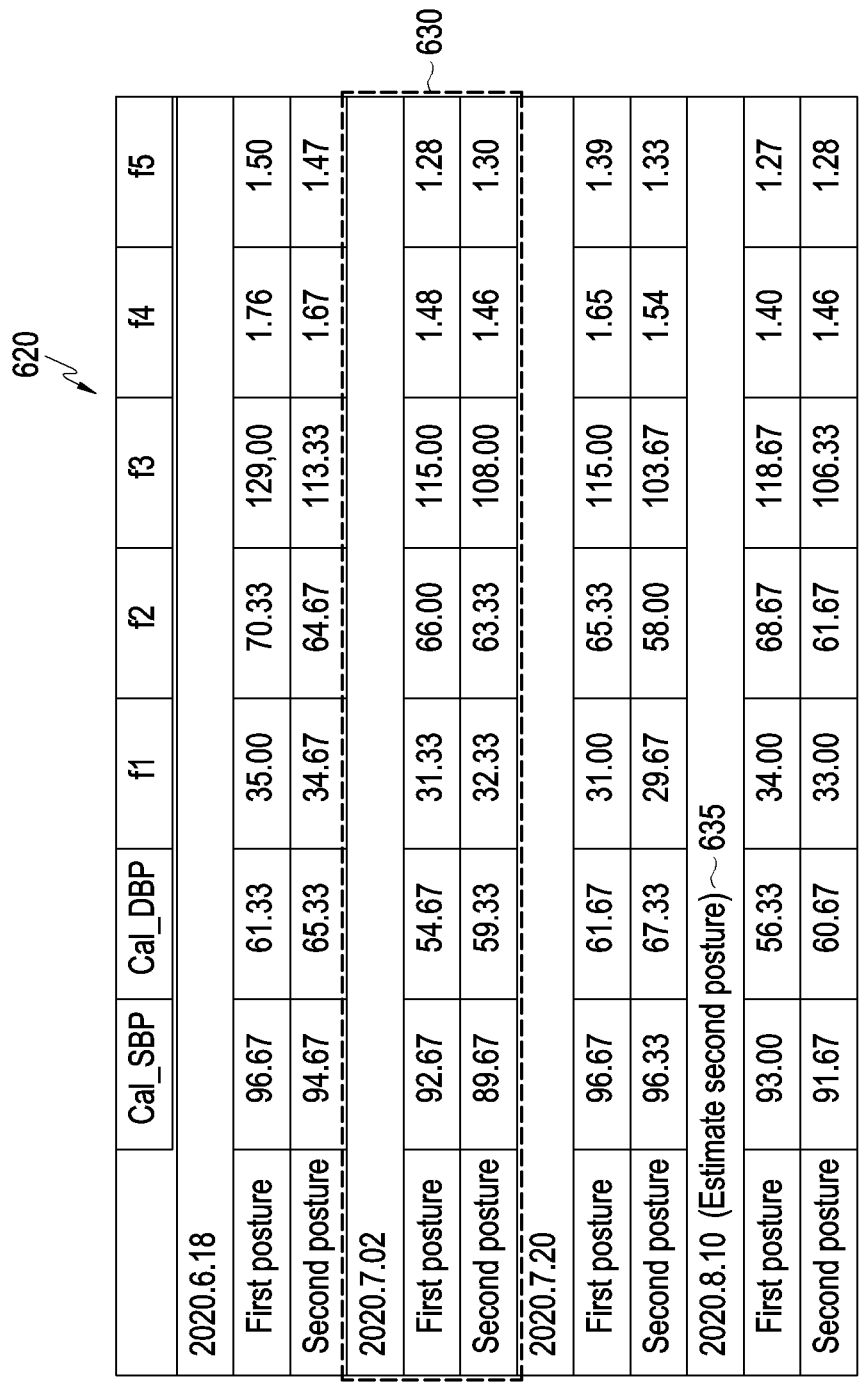

Referring to FIG. 6B, according to various embodiments, the wearable electronic device 201 may identify the calibration data set 630 having features matching the information 615 about the features of the first biometric signal 613 in the pre-stored calibration data sets 620. For example, the wearable electronic device 201 may compare the features of the biometric signals obtained in the first posture and the information 615 about the features of the first biometric signal 613 in each of the calibration data sets 620 and identify the calibration data set 630 having similar features to the information 615 about the features of the first biometric signal 613. For example, the calibration data set 630 can be selected based on a variety of measures, such as sum of squared distances, among others. The wearable electronic device 201 may identify a ratio between features of the biometric signal for the first posture and features of the biometric signal for the second posture from the identified calibration data set 630. The wearable electronic device 201 may identify a blood pressure difference between the blood pressure value for the first posture and the blood pressure value for the second posture from the identified calibration data set 630.

According to various embodiments, the wearable electronic device 201 may identify whether calibration information for the second posture is estimated from the pre-stored calibration data sets 620. If the calibration information for the second posture is estimated, the wearable electronic device 201 may add flag information 635 to the corresponding calibration data set. For example, the wearable electronic device 201 may identify, through the flag information 635, that the calibration information for the second posture obtained on "Aug. 10, 2020" is estimated information.

According to various embodiments, the wearable electronic device 201 may select, first, the calibration set obtained by directly measuring the calibration information for the second posture, in the pre-stored calibration data sets 620. For example, the wearable electronic device 201 may select, first, the calibration data set obtained by directly measuring both the first posture and the second posture, over the calibration set obtained by directly measuring the biometric signal and blood pressure value only in the first posture of the first posture and the second posture and estimating the features and blood pressure value of the biometric signal in the second posture.

Referring to FIG. 6C, according to various embodiments, the wearable electronic device 201 may estimate the features 640 of the second biometric signal obtainable in the second posture based on the identified ratio and the information 615 about the features of the first biometric signal 613.

Referring to FIG. 6D, according to various embodiments, the wearable electronic device 201 may analyze the values for the pre-stored calibration data sets 620 and identify an analysis result 650. For example, the wearable electronic device 201 may identify the average blood pressure value (e.g., average SBP and average DBP), maximum blood pressure value (e.g., maximum SBP and maximum DBP), and minimum blood pressure value (e.g., minimum SBP and minimum DBP) measured in the first posture and the average blood pressure value, maximum blood pressure value, and minimum blood pressure value measured in the second posture, in the pre-stored calibration data sets 620. The wearable electronic device 201 may estimate the second blood pressure value that may be measured in the second posture, considering the blood pressure difference between the blood pressure value for the first posture and the blood pressure value for the second posture, the difference between the average blood pressure value of the first posture and the average blood pressure value of the second posture, the maximum blood pressure value of the second posture, and the minimum blood pressure value of the second posture.

Referring to FIG. 6E, according to various embodiments, the wearable electronic device 201 may estimate information 660 about the second blood pressure value obtainable in the second posture. For example, when there is no or little difference between the SBP average blood pressure value of the first posture and the SBP average blood pressure value of the second posture (e.g., when the difference is less than a reference value), the wearable electronic device 201 may estimate the SBP of the second blood pressure value of the second posture as the same value (e.g., 93.67 mmHg) as the SBP of the first blood pressure value of the first posture. Further, when there is a meaningful difference between the DBP average blood pressure value of the first posture and the DBP average blood pressure value of the second posture (e.g., when the difference is the reference value or more), the wearable electronic device 201 may apply the difference (e.g., 4.66 mmHg) between the DBP blood pressure value of the first posture and the DBP blood pressure value of the second posture in the identified calibration data set 630 to the DBP (e.g., 60.33) of the first blood pressure value of the first posture, thereby estimating the DBP (e.g., 55.73 mmHg) of the second blood pressure value of the second posture. The wearable electronic device 201 may obtain the second calibration information 670 based on the information 660 about the second blood pressure value obtainable in the second posture and the features 640 of the second biometric signal obtainable in the second posture.

Figure 7:
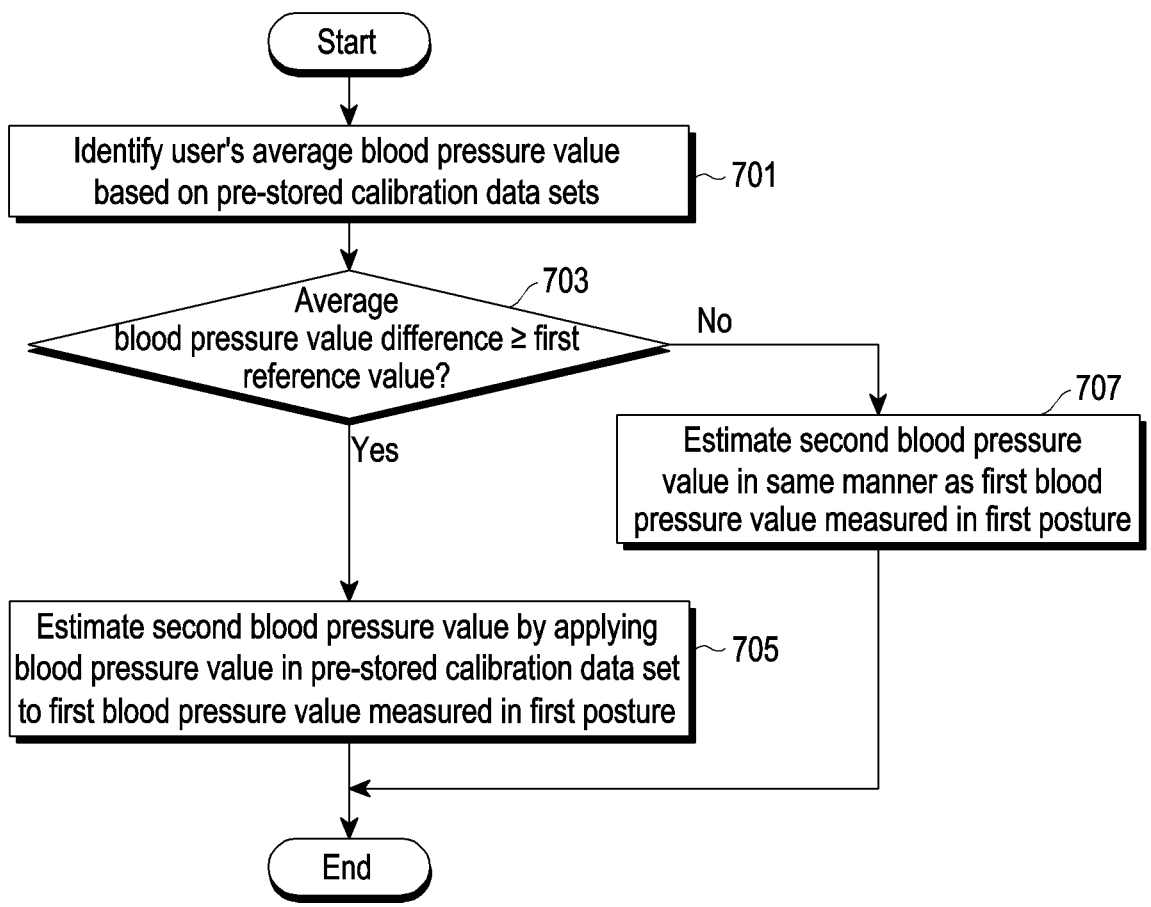
FIG. 7 is a flowchart illustrating a method for estimating a blood pressure value of a second posture based on an average blood pressure difference between a blood pressure value of a first posture and the blood pressure value of the second posture included in calibration data sets, by a wearable electronic device, according to various embodiments.

FIG. 7 is a flowchart illustrating a method for estimating a blood pressure value of a second posture based on an average blood pressure difference between a blood pressure value of a first posture and the blood pressure value of the second posture included in calibration data sets, by a wearable electronic device, according to various embodiments.

Referring to FIG. 7, according to various embodiments, in operation 701, the wearable electronic device 201 may identify a user's average blood pressure value based on the pre-stored calibration data sets. For example, the wearable electronic device 201 may identify the average blood pressure value (e.g., average SBP and average DBP) measured in the first posture and the average blood pressure value (e.g., average SBP and average DBP) (e.g., the analysis result 650 of FIG. 6D) measured in the second posture in the pre-stored calibration data sets (e.g., the calibration data sets 620 of FIG. 6B).

According to various embodiments, in operation 703, the wearable electronic device 201 may identify whether the difference between the average blood pressure value measured in the first posture and the average blood pressure value measured in the second posture is a first reference value or more. For example, the first reference value may be set automatically by the wearable electronic device 201 or by the user.

According to various embodiments, when the average blood pressure value difference is the first reference value or more (Yes in operation 703), in operation 705, the wearable electronic device 201 may estimate the second blood pressure value by applying the blood pressure value in the pre-stored calibration data set to the first blood pressure value measured in the first posture. For example, the wearable electronic device 201 may estimate the second blood pressure value of the second posture by applying the difference between the blood pressure value of the first posture and the blood pressure value of the second posture to the first blood pressure value in the identified calibration data set (e.g., the calibration data set having features matching the features of the first biometric signal obtained through the first sensor) among the pre-stored calibration data sets.

According to various embodiments, when the average blood pressure value difference is less than the first reference value (No in operation 703), in operation 707, the wearable electronic device 201 may estimate the second blood pressure value, like the first blood pressure value measured in the first posture. For example, when the average blood pressure value difference is less than the first reference value, the wearable electronic device 201 may determine that there is no or little difference between the blood pressure values measured in the first posture and the second posture and estimate the same value as the first blood pressure value, as the second blood pressure value.

Figure 8:
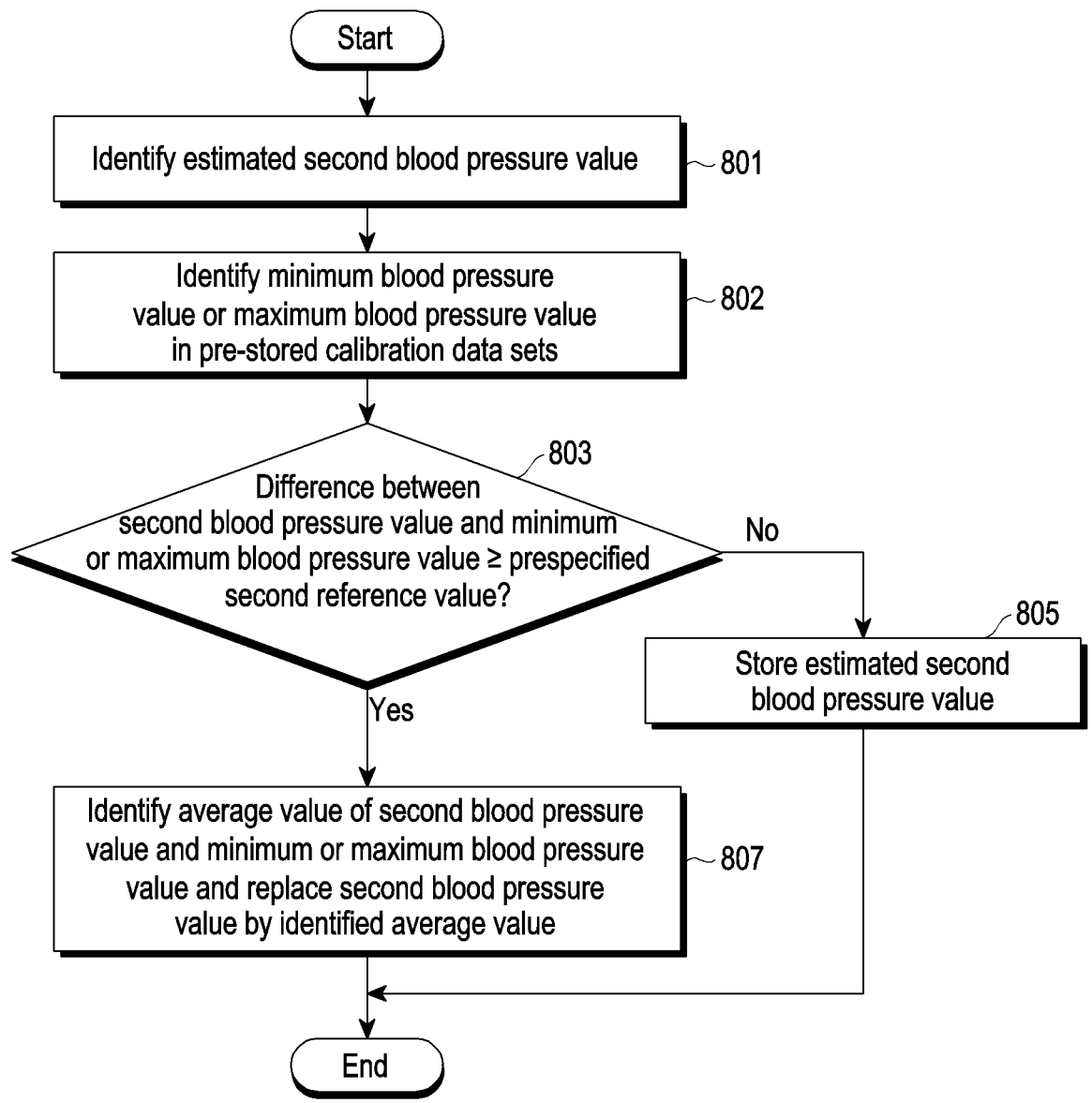
FIG. 8 is a flowchart illustrating another method for estimating a blood pressure value of a second posture estimated, by a wearable electronic device, according to various embodiments.

FIG. 8 is a flowchart illustrating another method for estimating a blood pressure value of a second posture estimated, by a wearable electronic device, according to various embodiments.

Referring to FIG. 8, according to various embodiments, in operation 801, the wearable electronic device 201 may identify the estimated second blood pressure value.

According to various embodiments, in operation 802, the wearable electronic device 201 may identify the minimum blood pressure value or maximum blood pressure value measured in the second posture in the pre-stored calibration data sets.

According to various embodiments, in operation 803, the wearable electronic device 201 may identify whether the difference between the estimated second blood pressure value and the minimum blood pressure value (or maximum blood pressure value) is a specific second reference value or more. For example, the second reference value may be set automatically by the wearable electronic device 201 or by the user.

According to various embodiments, when the difference between the estimated second blood pressure value and the minimum blood pressure value (or the maximum blood pressure value) is less than the specific second reference value (No in operation 803), in operation 805, the wearable electronic device 201 may store the estimated second blood pressure value as the second calibration information. In other words, the wearable electronic device 201 may store the estimated second blood pressure value in the memory 230.

According to various embodiments, when the difference between the estimated second blood pressure value and the minimum blood pressure value (or maximum blood pressure value) is the specific second reference value or more (Yes in operation 803), in operation 807, the wearable electronic device 201 may identify the average value of the second blood pressure value and the minimum blood pressure value (or maximum blood pressure value) of the pre-stored calibration data sets and replace the second blood pressure value by the identified average value or identify the identified average value as the second blood pressure value.

According to various embodiments, when the difference between the estimated second blood pressure value and the minimum blood pressure value (or maximum blood pressure value) is equal to or larger than a third reference value larger than the specific second reference value, a message to request the user to re-measure blood pressure for calibration data may be displayed. For example, since there may be an error in estimation of the second blood pressure value or the user may be in a poor health condition, the wearable electronic device 201 may request the user to directly measure blood pressure in the second posture by displaying the message.

Figure 9:
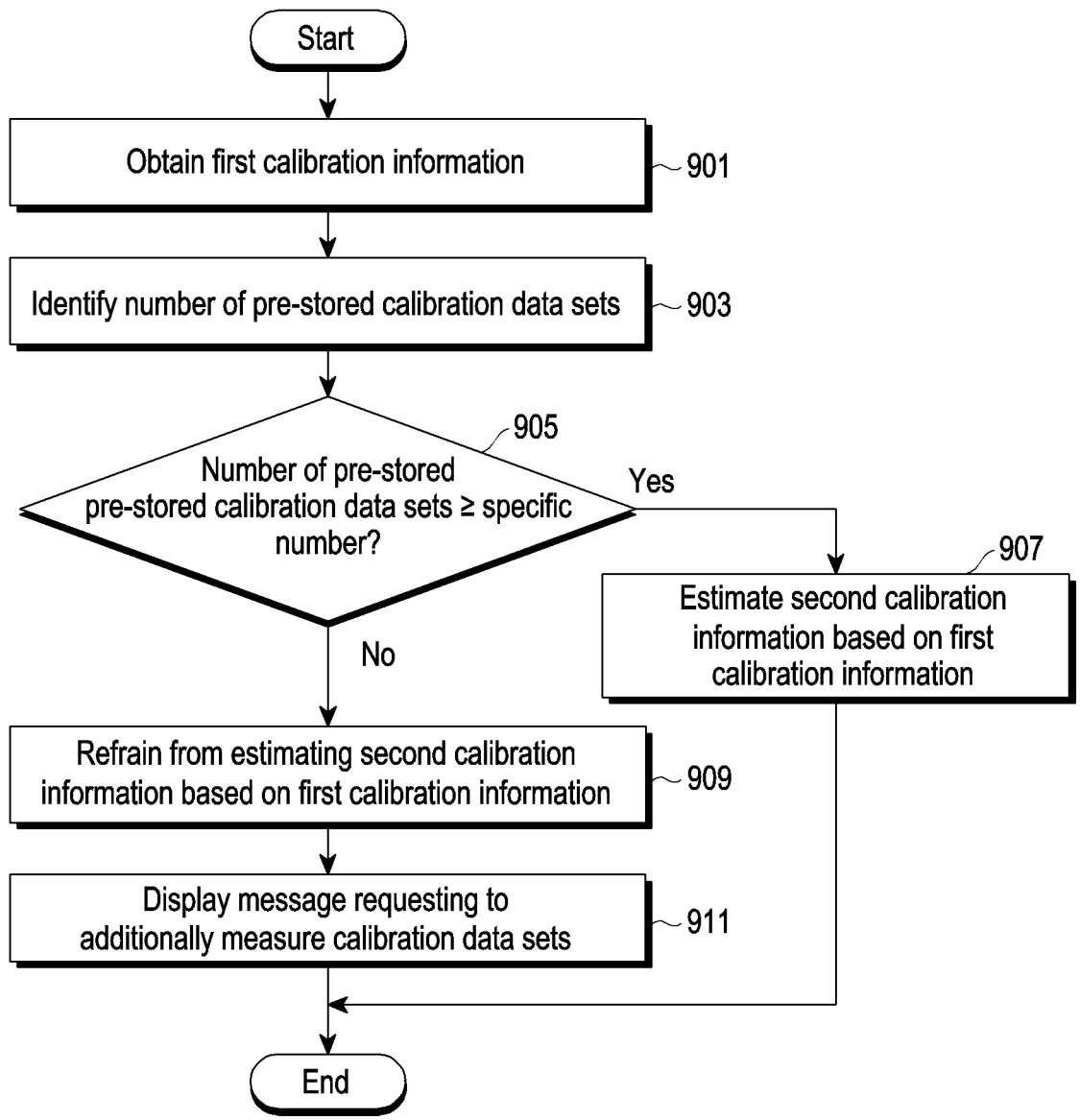
FIG. 9 is a flowchart illustrating an operation for identifying whether a condition for estimating second calibration information is met using first calibration information by a wearable electronic device according to various embodiments.

FIG. 9 is a flowchart illustrating an operation for identifying whether a condition for estimating second calibration information is met using first calibration information by a wearable electronic device according to various embodiments.

Referring to FIG. 9, according to various embodiments, in operation 901, the wearable electronic device 201 may obtain first calibration information about the first posture (e.g., the first calibration information 610 of FIG. 6A).

According to various embodiments, in operation 903, the wearable electronic device 201 may identify the number of pre-stored calibration data sets (e.g., the calibration data sets 620 of FIG. 6B) before estimating the second calibration information about the second posture.

According to various embodiments, in operation 905, the wearable electronic device 201 may identify whether the number of pre-stored calibration data sets is larger than or equal to a specific number (e.g., five). For example, the specific number may be set automatically by the wearable electronic device 201 or by the user.

According to various embodiments, when the number of pre-stored calibration data sets is equal to or larger than the specific number (Yes in operation 905), in operation 907, the wearable electronic device 201 may estimate the second calibration information (e.g., the second calibration information 670 of FIG. 6E) based on the first calibration information according to the above-described method.

According to various embodiments, when the number of pre-stored calibration data sets is less than the specific number (No in operation 905), in operation 909, the wearable electronic device 201 may not estimate the second calibration information based on the first calibration information.

According to various embodiments, in operation 911, the wearable electronic device 201 may display a message requesting the user to additionally measure calibration data sets. In other words, when the number of calibration data sets is less than the specific number, reliability and accuracy may decrease. Thus, the wearable electronic device 201 may not estimate the second calibration information about the second posture based on the first calibration information for the first posture.

FIGS. 10A to 10D are views illustrating a user interface provided by an electronic device according to various embodiments.

Referring to FIGS. 10A to 10D, according to various embodiments, an electronic device 1004 may be implemented in substantially the same or similar manner to the electronic device 204 described in connection with FIG. 2. The electronic device 1004 may be connected to the wearable electronic device 201 and the external blood pressure monitor 202 through a communication module (e.g., the communication module 190 of FIG. 1) included in the electronic device 1004. Further, the electronic device 1004 may receive data measured by the wearable electronic device 201 and the external blood pressure monitor 202 and may display screens related to the operation of securing data for calibrating the user's blood pressure based on the received data. For example, electronic device 1004 may be paired with the wearable electronic device 204 and the external blood pressure monitor 202 via a Bluetooth connection. Alternatively, the blood pressure monitor 202 may connect to the electronic device 1004 via a USB chord.

Figure 10A:
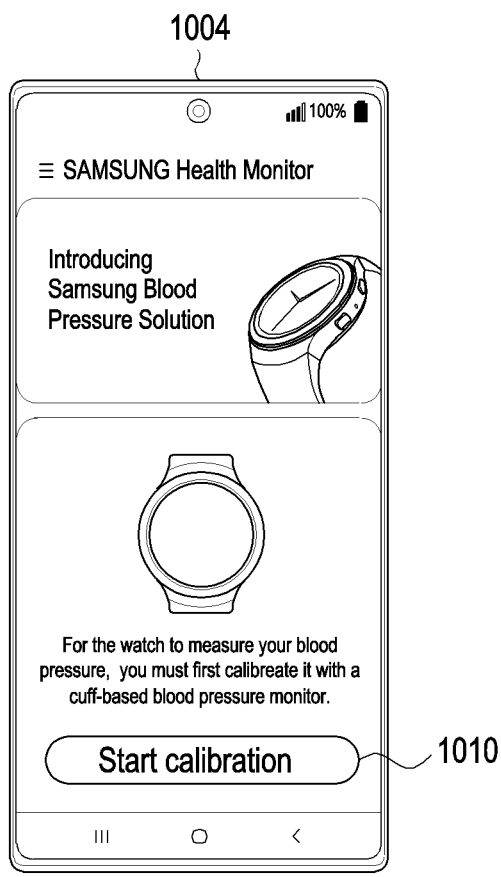
FIGS. 10A to 10D are views illustrating a user interface provided by an electronic device according to various embodiments.

Referring to FIG. 10A, according to various embodiments, the electronic device 1004 may display a first screen for a calibration operation for blood pressure monitoring. The electronic device 1004 may display a first object 1010 for starting the calibration operation on the first screen. Further, the electronic device 1004 may display a brief description of the calibration operation together on the first screen.

Figure 10B:
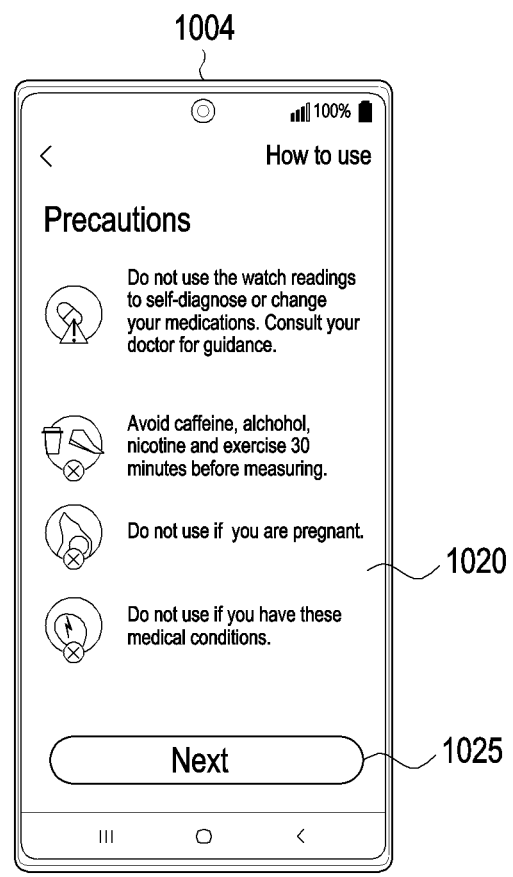

Referring to FIG. 10B, when a user input to the first object 1010 is identified, the electronic device 1004 may display a second screen 1020 for a caution before starting a calibration operation. The electronic device 1004 may display a second object 1025 for performing a calibration operation on the second screen 1020.

Figure 10C:
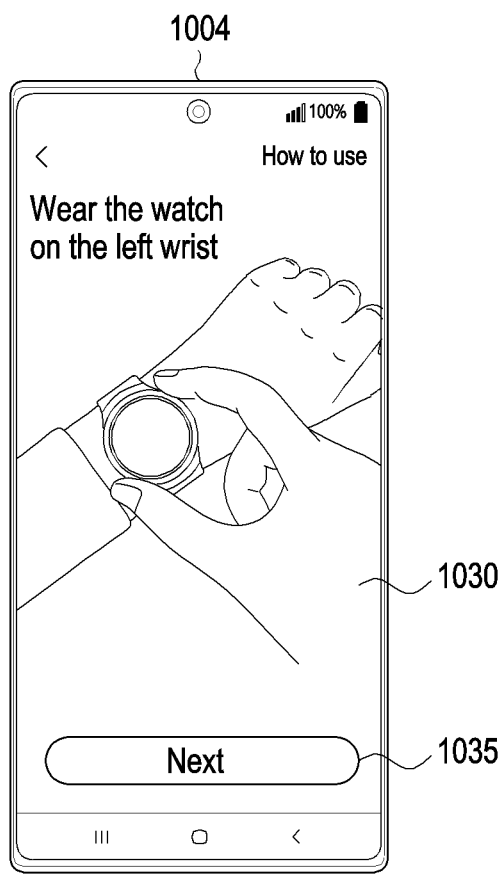

Referring to FIG. 10C, if a user input to the second object 1025 is identified, the electronic device 1004 may display a third screen 1030 describing how to wear the wearable electronic device 201 before starting a calibration operation. The electronic device 1004 may display a third object 1035 for performing a calibration operation on the third screen 1030.

Figure 10D:
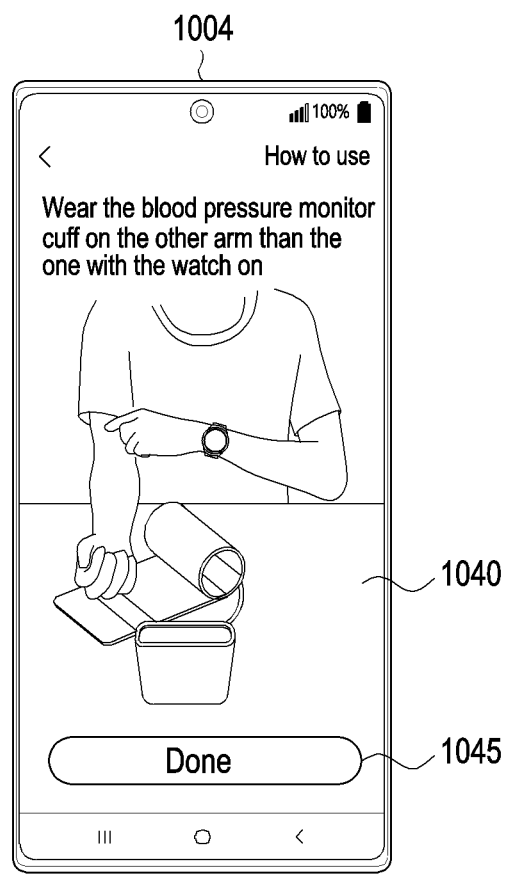

Referring to FIG. 10D, if a user input to the third object 1035 is identified, the electronic device 1004 may display a fourth screen 1040 describing how to wear an external blood pressure monitor 202 (e.g., a blood pressure monitor including a cuff) before starting a calibration operation. The electronic device 1004 may display a fourth object 1045 for completing a calibration preparation operation on the fourth screen 1040. If a user input to the fourth object 1045 is identified, the electronic device 1004 may display screens for completing the calibration preparation operation and obtaining data for calibration. Referring to FIGS. 10C and 10D generally guide the user to measure their blood pressure using both the wearable electronic device 204 and the external blood pressure monitor 202, substantially simultaneously.

FIGS. 11A to 11G are views illustrating a user interface provided by an electronic device according to various embodiments.

Figure 11A:
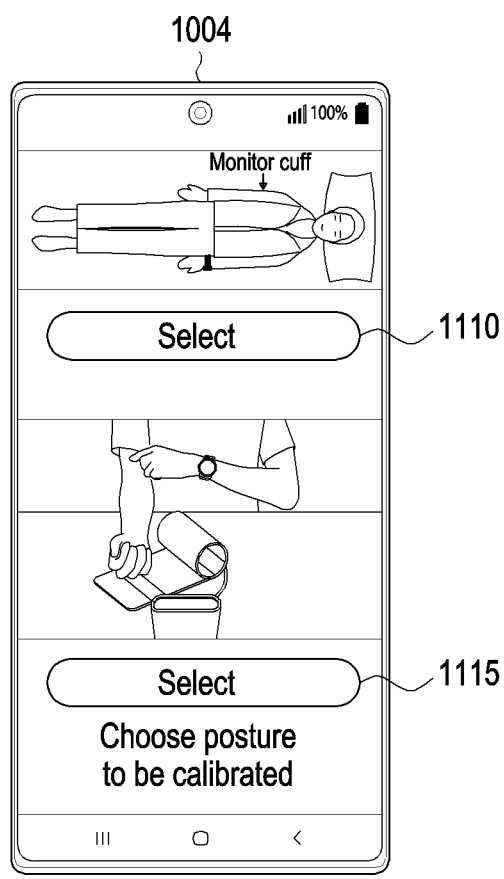
FIGS. 11A to 11G are views illustrating a user interface provided by an electronic device according to various embodiments.

Referring to FIG. 11A, the electronic device 1004 may display a first screen for selecting a posture for obtaining calibration data. The first screen may include a first object 1110 for selecting a first posture (e.g., a lying posture) and a second object 1115 for selecting a second posture (e.g., a sitting posture). Meanwhile, FIG. 11A only illustrates a screen for selecting two postures for convenience of description, but the present invention may not be limited thereto. For example, the electronic device 1004 may display a first screen for selecting a plurality of postures and may further include an object for selecting an additional posture.

Figure 11B:
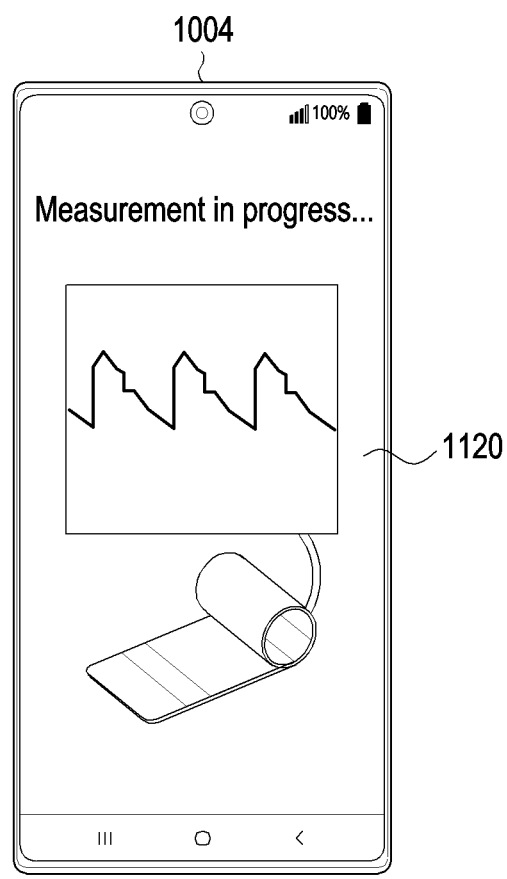

Referring to FIG. 11B, if a user input to the second object 1115 is identified, the electronic device 1004 may display a second screen 1120 indicating a state of obtaining calibration data in the second posture.

Figure 11C:
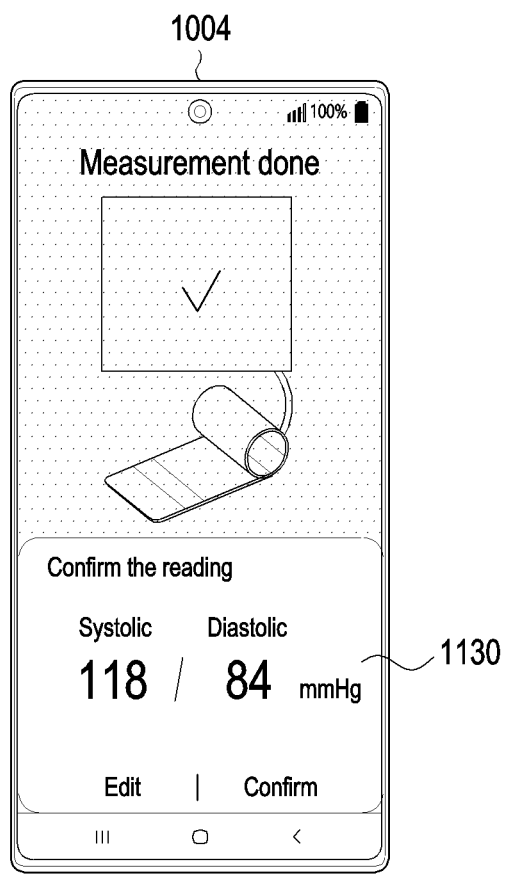

Referring to FIG. 11C, if obtaining the calibration data in the second posture is completed, the electronic device 1004 may receive the user's blood pressure value measured by the external blood pressure monitor 202 and may display a third screen indicating completion of the measurement. For example, the third screen may include information 1130 about the result of measuring the user's blood pressure measured by the external blood pressure monitor 202. According to an embodiment, the electronic device 1004 may guide the user to obtain calibration data about three times in the second posture.

Figure 11D:
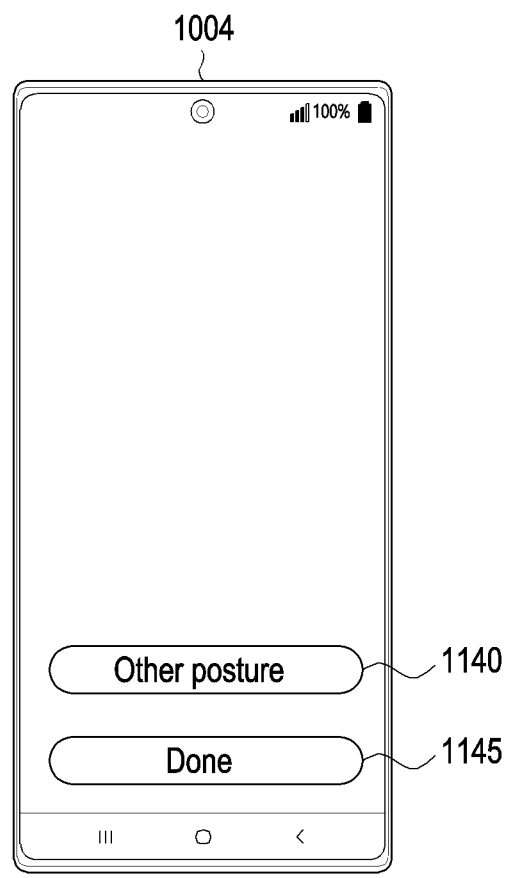

Referring to FIG. 11D, after displaying the information 1130 about the result of measuring the user's blood pressure, the electronic device 1004 may display a fourth screen including a third object 1140 for continuously measuring the user's blood pressure in another posture and a fourth object 1145 for terminating the measurement of blood pressure. If a user input to the fourth object 1145 is identified, the electronic device 1004 may store the measured blood pressure value and terminate the blood pressure measurement to obtain calibration data.

According to various embodiments, When a user input to the third object 1140 is identified, the electronic device 1004 may display a first screen for selecting the posture to obtain the calibration data shown in FIG. 11A. According to another embodiment, as shown in FIG. 11A, when the electronic device 1004 only supports the operation of obtaining calibration data for two postures, if a user input to the third object 1140 is identified, the electronic device 1004 may display a screen (e.g., the fifth screen 1150) indicating the state of obtaining calibration data in the first posture. For example, if a user input to the third object 1140 is identified, the electronic device 1004 may provide a message indicating the start of measurement of calibration data in the first posture.

Figure 11E:
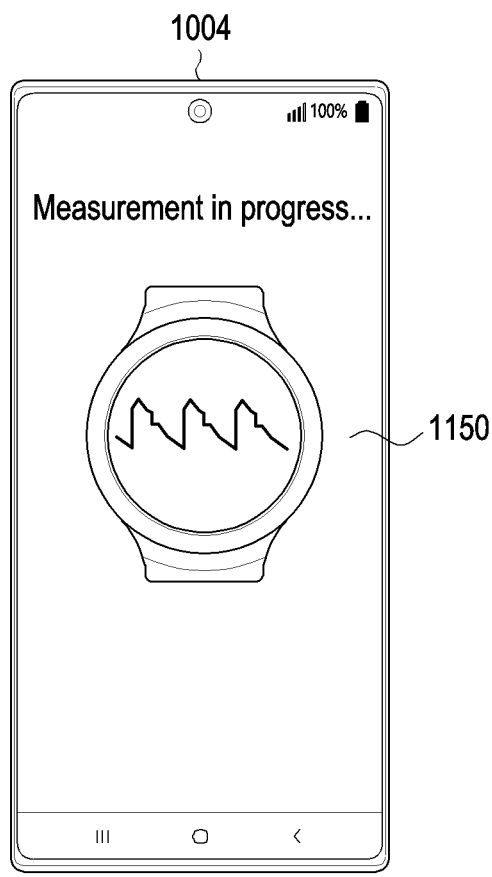

Referring to FIG. 11E, if a user input to the first object 1110 is identified, the electronic device 1004 may display a fifth screen 1150 indicating a state of obtaining calibration data in the first posture.

Figure 11F:
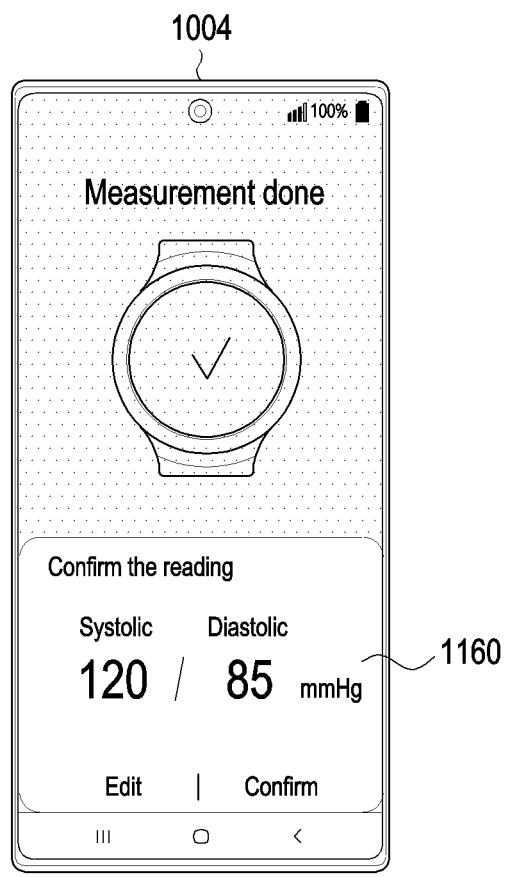

Referring to FIG. 11F, if obtaining the calibration data in the first posture is completed, the electronic device 1004 may display a sixth screen indicating completion of the measurement. For example, the sixth screen may include information 1160 about the result of measuring the user's blood pressure measured by the external blood pressure monitor 202.

Figure 11G:
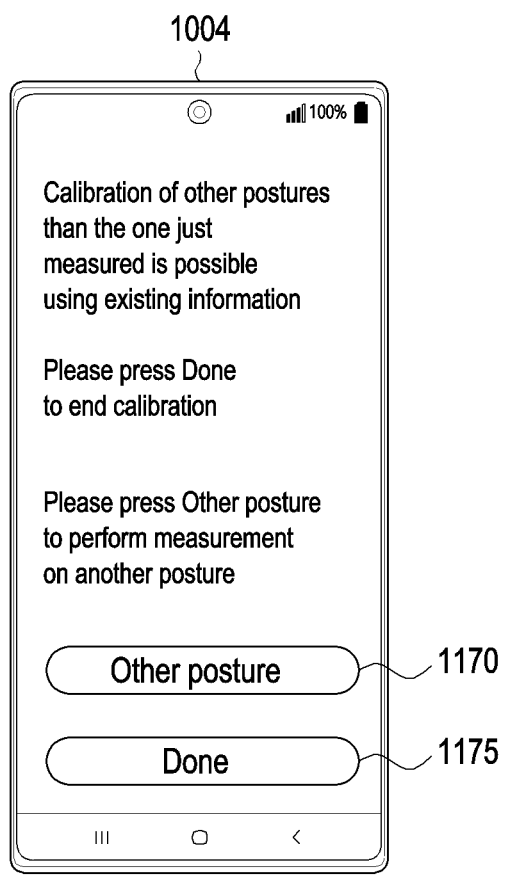

Referring to FIG. 11G, after displaying the information 1160 about the result of measuring the user's blood pressure, the electronic device 1004 may display a seventh screen including a fifth object 1170 for continuously measuring the user's blood pressure in another posture and a sixth object 1175 for terminating the measurement of blood pressure. If a user input to the sixth object 1175 is identified, the electronic device 1004 may store the measured blood pressure value and terminate the operation of obtaining calibration data. According to an embodiment, if the number of pre-stored calibration data sets is larger than or equal to a designated number, the electronic device 1004 may display a screen including a message indicating that calibration data may be obtained for another posture without additional measurement only with the calibration data for one posture measured.

FIGS. 12A to 12E are views illustrating a user interface provided by a wearable electronic device according to various embodiments.

Referring to FIGS. 12A to 12E, according to various embodiments, an electronic device 1201 may be implemented in substantially the same or similar manner to the electronic device 201 described in connection with FIG. 2. The wearable electronic device 1201 may display screens related to an operation for securing data for calibrating the user's blood pressure. For example, the wearable electronic device 1201 may receive data measured by an external blood pressure monitor 202 without an electronic device 204 or 1004 and display screens related to the operation of securing data for calibrating the user's blood pressure.

Figure 12A:
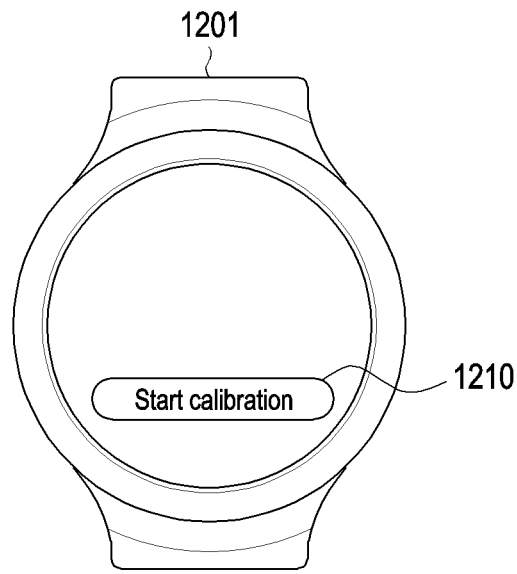
FIGS. 12A to 12E are views illustrating a user interface provided by a wearable electronic device according to various embodiments.

Referring to FIG. 12A, according to various embodiments, the wearable electronic device 1201 may display a first screen for starting a calibration operation for blood pressure monitoring. The wearable electronic device 1201 may display a first object 1210 for starting the calibration operation on the first screen. Further, the wearable electronic device 1201 may display a brief description of the calibration operation together on the first screen.

Figure 12B:
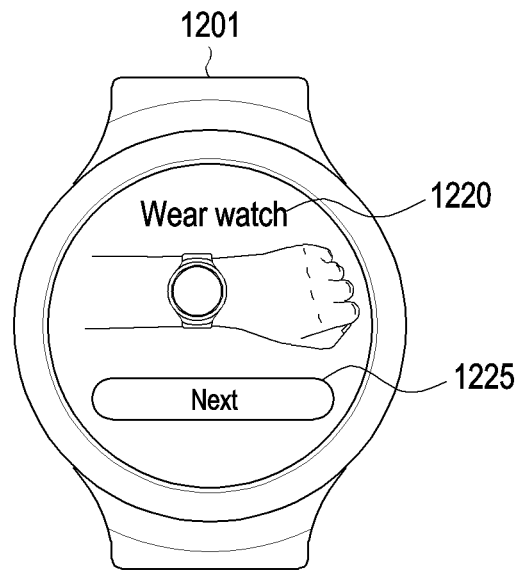

Referring to FIG. 12B, if a user input to the first object 1210 is identified, the wearable electronic device 1201 may display a second screen 1220 describing how to wear the wearable electronic device 1201 before starting a calibration operation. The wearable electronic device 1201 may display a second object 1225 for performing a calibration operation on the second screen 1220.

Figure 12C:
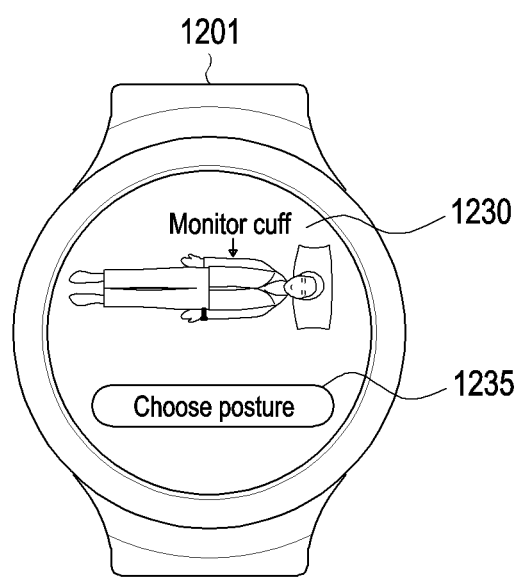

Referring to FIG. 12C, if a user input to the second object 1225 is identified, the wearable electronic device 1201 may display a third screen 1230 for selecting the posture of obtaining calibration data. The third screen 1230 may include a third object 1235 for selecting a posture for measuring a blood pressure value.

Figure 12D:
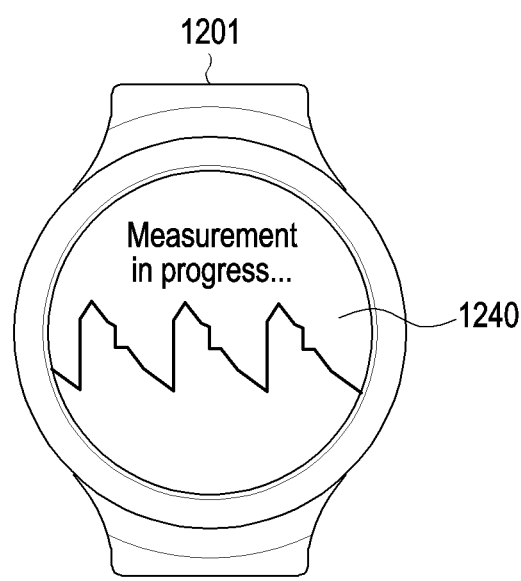

Referring to FIG. 12D, if a user input to the third object 1235 is identified, the wearable electronic device 1201 may display a fourth screen 1240 indicating the state of obtaining calibration data by the wearable electronic device 1201 in the selected posture.

Figure 12E:
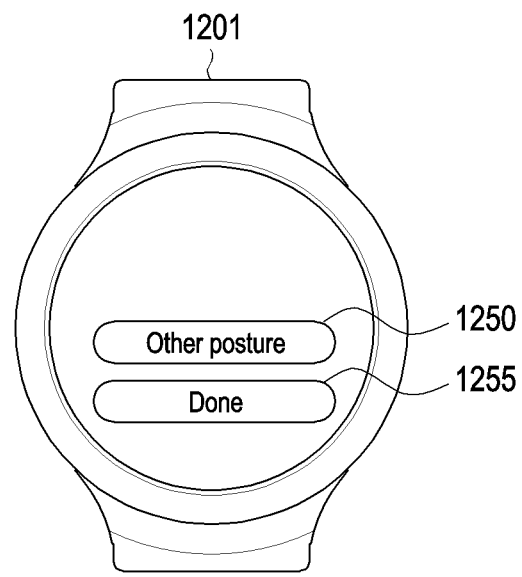

Referring to FIG. 12E, if obtaining calibration data is completed in the selected posture, the wearable electronic device 1201 may display a fifth screen indicating the completion of measurement although not shown in the drawings. For example, the fifth screen may include information about the result of measuring the user's blood pressure measured by the external blood pressure monitor 202. The wearable electronic device 1201 may display a sixth screen including a fourth object 1250 for continuously measuring the user's blood pressure in another posture and a fifth object 1255 for terminating the measurement of blood pressure. If a user input to the fourth object 1250 is identified, the wearable electronic device 1201 may display a third screen for selecting the posture shown in FIG. 12C. Alternatively, if a user input to the fifth object 1255 is identified, the wearable electronic device 1201 may store the measured blood pressure value and terminate the operation of obtaining calibration data.

According to various embodiments, a wearable electronic device (e.g., the wearable electronic device 201 of FIG. 2) may comprise a memory (e.g., the memory 230 of FIG. 2), a first sensor (e.g., the first sensor 240 of FIG. 2), a second sensor (e.g., the second sensor 250 of FIG. 2), and a processor (e.g., the processor 220 of FIG. 2). The processor may be configured to, obtain a user's first biometric signal in a user's first posture through the first sensor, obtain, from an external electronic device, information about a user's first blood pressure value measured by the external electronic device in the first posture, obtain first calibration information for quantifying first blood pressure information measured in the first posture, based on information about features of the first biometric signal and the first blood pressure value, identify whether calibration data sets for a plurality of postures of the user, pre-stored in the memory, meet a specific condition for estimating second calibration information for quantifying second blood pressure information measured in a user's second posture, and when the calibration data sets meet the specific condition, estimate the second calibration information based on the calibration data sets and the first calibration information.

The processor may be configured to identify first calibration data of the first posture matching the features of the first biometric signal among calibration data sets for the user's first posture pre-stored in the memory, identify second calibration data of the second posture corresponding to the first calibration data of the first posture, identify a difference between the first calibration data and the second calibration data, and estimate the second calibration information including information about features of a second biometric signal and a second blood pressure value, obtainable in the second posture, based on the features of the first biometric signal, the first blood pressure value, and the difference.

The processor may be configured to identify a ratio between features of a biometric signal measured in the first posture, included in the first calibration data and features of a biometric signal measured in the second posture, included in the second calibration data and estimate the features of the second biometric signal obtainable in the second posture by applying the ratio to the features of the first biometric signal.

The processor may be configured to identify a difference value between a blood pressure value measured in the first posture, included in the first calibration data, and a blood pressure value measured in the second posture, included in the second calibration data and estimate the second blood pressure value obtainable in the second posture based on the first blood pressure value and the difference value.

The processor may be configured to identify an average blood pressure difference between blood pressure values of the first posture and blood pressure values of the second posture, included in the calibration data sets for the plurality of postures and if the average blood pressure difference is smaller than a first reference value, estimate the same value as the first blood pressure value as the second blood pressure value.

The processor may be configured to, when a difference between a first value obtained by applying the difference value to the first blood pressure value and a minimum blood pressure value included in the calibration data sets is a second reference value or more, identify an average value of the first value and the minimum blood pressure value as the second blood pressure value.

The processor may be configured to, when a difference between a second value obtained by applying the difference value to the first blood pressure value and a maximum blood pressure value included in the calibration data sets is a second reference value or more, identify an average value of the second value and the maximum blood pressure value as the second blood pressure value.

The processor may be configured to, when a difference between a first value obtained by applying the difference value to the first blood pressure value and a minimum blood pressure value included in the calibration data sets is a second reference value or more or when a difference between a second value obtained by applying the difference value to the first blood pressure value and a maximum blood pressure value included in the calibration data sets is the second reference value or more, display, on a display of the wearable electronic device, a message requesting to re-measure blood pressure information for calibration information related to the second posture.

The processor may be configured to, when the number of the plurality of calibration data sets is less than a specific number, refrain from estimating the second calibration information.

The processor may be configured to identify the user's third blood pressure information based on the user's third biometric signal obtained through the first sensor, in response to a command to measure the user's blood pressure, identify the user's posture when a third biometric signal is obtained, through the second sensor, identify calibration information about the identified posture of the user among calibration data sets including the first calibration data set stored in the memory, calibrate the third blood pressure information, based on the calibration information, and display, on a display of the wearable electronic device, information about the user's third blood pressure value quantified based on the calibrated third blood pressure information.

The processor may be configured to obtain information about the third blood pressure value using a method different from a method in which the external electronic device measures the information about the first blood pressure value.

According to various embodiments, a method for operating a wearable electronic device (e.g., the wearable electronic device 201 of FIG. 2) may comprise, obtaining a user's first biometric signal in a user's first posture through a first sensor (e.g., the first sensor 240 of FIG. 2) included in the wearable electronic device, obtaining, from an external electronic device, information about a user's first blood pressure value measured by the external electronic device in the first posture, obtaining first calibration information for quantifying first blood pressure information measured in the first posture, based on information about features of the first biometric signal and the first blood pressure value, identifying whether calibration data sets for a plurality of postures of the user, pre-stored in the electronic device, meet a specific condition for estimating second calibration information for quantifying second blood pressure information measured in a user's second posture, and when the calibration data sets meet the specific condition, estimating the second calibration information based on the calibration data sets and the first calibration information.

Estimating the second calibration information may include identifying first calibration data of the first posture matching the features of the first biometric signal among first calibration data sets for the user's first posture pre-stored in the wearable electronic device, identifying second calibration data of the second posture corresponding to the first calibration data of the first posture, identifying a difference between the first calibration data and the second calibration data, and estimating the second calibration information including information about features of a second biometric signal and a second blood pressure value, obtainable in the second posture, based on the features of the first biometric signal, the first blood pressure value, and the difference.

Estimating the second calibration information may include identifying a ratio between features of a biometric signal measured in the first posture, included in the first calibration data and features of a biometric signal measured in the second posture, included in the second calibration data and estimating the features of the second biometric signal obtainable in the second posture by applying the ratio to the features of the first biometric signal.

Estimating the second calibration information may include identifying a difference value between a blood pressure value measured in the first posture, included in the first calibration data, and a blood pressure value measured in the second posture, included in the second calibration data and estimating the second blood pressure value obtainable in the second posture based on the first blood pressure value and the difference value.

Estimating the second blood pressure value may include identifying an average blood pressure difference between blood pressure values of the first posture and blood pressure values of the second posture, included in the calibration data sets for the plurality of postures and when the average blood pressure difference is smaller than a first reference value, estimating the same value as the first blood pressure value as the second blood pressure value.

Estimating the second blood pressure value may include, when a difference between a first value obtained by applying the difference value to the first blood pressure value and a minimum blood pressure value included in the calibration data sets is a second reference value or more, determining an average value of the first value and the minimum blood pressure value as the second blood pressure value.

Estimating the second blood pressure value may include, when a difference between a second value obtained by applying the difference value to the first blood pressure value and a maximum blood pressure value included in the calibration data sets is a second reference value or more, identifying an average value of the second value and the maximum blood pressure value as the second blood pressure value.

The method may further comprise identifying the number of the plurality of calibration data sets and, when the number of the plurality of calibration data sets is less than a specific number, displaying a message requesting to measure a blood pressure value for calibration in the second posture without performing the estimation of the second calibration information.

According to various embodiments, an electronic device (e.g., the electronic device 204 of FIG. 2) may comprise a memory, a communication module, and a processor. The processor may be configured to obtain information about a user's first biometric signal measured in a user's first posture from a wearable electronic device, through the communication module, obtain, from the external electronic device, information about the user's first blood pressure value measured by the external electronic device in the first posture, through the communication module, obtain first calibration information for quantifying first blood pressure information measured in the first posture, based on information about features of the first biometric signal and the first blood pressure value, identify whether calibration data sets for a plurality of postures of the user, pre-stored in the memory, meet a specific condition for estimating second calibration information for quantifying second blood pressure information measured in a user's second posture, and when the calibration data sets meet the specific condition, estimate the second calibration information based on the calibration data sets and the first calibration information.

Although the foregoing embodiments are described a degree of particularity, it shall be understood that this disclosure is not limited to the foregoing embodiments, and moreover, features of the foregoing embodiment can be removed, added, or modified, without depart from the scope of this disclosure, as set for in the following claims, and equivalents thereof.

The invention claimed is:

1. A wearable electronic device comprising:
a memory;
a first sensor;
a second sensor; and
a processor,
wherein the processor is configured to,
obtain a user's first biometric signal in a user's first posture through the first sensor,
obtain, from an external electronic device, information about a user's first blood pressure value measured by the external electronic device in the first posture,
obtain first calibration information for quantifying first blood pressure information measured in the first posture, based on information about features of the first biometric signal and the first blood pressure value,
identify whether calibration data sets for a plurality of postures of the user, pre-stored in the memory, meet a specific condition for estimating second calibration information for quantifying second blood pressure information measured in a user's second posture, and
when the calibration data sets meet the specific condition, estimate the second calibration information based on the calibration data sets and the first calibration information.

2. The wearable electronic device of claim 1, wherein the processor is configured to,
identify first calibration data of the first posture matching the features of the first biometric signal among calibration data sets for the user's first posture pre-stored in the memory,
identify second calibration data of the second posture corresponding to the first calibration data of the first posture,
identify a difference between the first calibration data and the second calibration data, and
estimate the second calibration information including information about features of a second biometric signal and a second blood pressure value, obtainable in the second posture, based on the features of the first biometric signal, the first blood pressure value, and the difference.

3. The wearable electronic device of claim 2, wherein the processor is configured to,
identify a ratio between features of a biometric signal measured in the first posture included in the first calibration data and features of a biometric signal measured in the second posture, included in the second calibration data, and
estimate the features of the second biometric signal obtainable in the second posture by applying the ratio to the features of the first biometric signal.

4. The wearable electronic device of claim 2, wherein the processor is configured to,
identify a difference value between a blood pressure value measured in the first posture included in the first calibration data, and a blood pressure value measured in the second posture, included in the second calibration data, and
estimate the second blood pressure value obtainable in the second posture based on the first blood pressure value and the difference value.

5. The wearable electronic device of claim 4, wherein the processor is configured to,
identify an average blood pressure difference between blood pressure values of the first posture and blood pressure values of the second posture, included in the calibration data sets for the plurality of postures, and
when the average blood pressure difference is smaller than a first reference value, estimate the same value as the first blood pressure value as the second blood pressure value.

6. The wearable electronic device of claim 4, wherein the processor is configured to, when a difference between a first value obtained by applying the difference value to the first blood pressure value and a minimum blood pressure value included in the calibration data sets is a second reference value or more, identify an average value of the first value and the minimum blood pressure value as the second blood pressure value.

7. The wearable electronic device of claim 4, wherein the processor is configured to, when a difference between a second value obtained by applying the difference value to the first blood pressure value and a maximum blood pressure value included in the calibration data sets is a second reference value or more, identify an average value of the second value and the maximum blood pressure value as the second blood pressure value.

8. The wearable electronic device of claim 4, wherein the processor is configured to, when a difference between a first value obtained by applying the difference value to the first blood pressure value and a minimum blood pressure value included in the calibration data sets is a second reference value or more or when a difference between a second value obtained by applying the difference value to the first blood pressure value and a maximum blood pressure value included in the calibration data sets is the second reference value or more, display, on a display of the wearable electronic device, a message requesting to re-measure blood pressure information for calibration information related to the second posture.

9. The wearable electronic device of claim 1, wherein the processor is configured to, when the number of the plurality of calibration data sets is less than a specific number, refrain from estimating the second calibration information.

10. The wearable electronic device of claim 1, wherein the processor is configured to,
identify a user's third blood pressure information based on a user's third biometric signal obtained through the first sensor, in response to a command to measure a user's blood pressure,
identify the user's posture when the third biometric signal is obtained, through the second sensor,
identify calibration information about the identified posture of the user among calibration data sets including the first calibration data set stored in the memory,
calibrate the third blood pressure information, based on the calibration information, and
display, on a display of the wearable electronic device, information about the user's third blood pressure value quantified based on a calibrated third blood pressure information.

11. The wearable electronic device of claim 10, wherein the processor is configured to obtain information about the third blood pressure value using a method different from a method in which the external electronic device measures the information about the first blood pressure value.

12. A method for operating a wearable electronic device, the method comprising:
obtaining a user's first biometric signal in a user's first posture through a first sensor included in the wearable electronic device;
obtaining, from an external electronic device, information about a user's first blood pressure value measured by the external electronic device in the first posture;
obtaining first calibration information for quantifying first blood pressure information measured in the first posture, based on information about features of the first biometric signal and the first blood pressure value;
identifying whether calibration data sets for a plurality of postures of the user, pre-stored in the electronic device, meet a specific condition for estimating second calibration information for quantifying second blood pressure information measured in a user's second posture; and
when the calibration data sets meet the specific condition, estimating the second calibration information based on the calibration data sets and the first calibration information.

13. The method of claim 12, wherein estimating the second calibration information comprises,
identifying first calibration data of the first posture matching the features of the first biometric signal among first calibration data sets for the user's first posture pre-stored in the wearable electronic device;
identifying second calibration data of the second posture corresponding to the first calibration data of the first posture;
identifying a difference between the first calibration data and the second calibration data; and
estimating the second calibration information including information about features of a second biometric signal and a second blood pressure value, obtainable in the second posture, based on the features of the first biometric signal, the first blood pressure value, and the difference.

14. The method of claim 13, wherein estimating the second calibration information comprises,
identifying a ratio between features of a biometric signal measured in the first posture, included in the first calibration data and features of a biometric signal measured in the second posture, included in the second calibration data; and
estimating the features of the second biometric signal obtainable in the second posture by applying the ratio to the features of the first biometric signal.

15. The method of claim 13, wherein estimating the second calibration information comprises,
identifying a difference value between a blood pressure value measured in the first posture, included in the first calibration data, and a blood pressure value measured in the second posture, included in the second calibration data; and
estimating the second blood pressure value obtainable in the second posture based on the first blood pressure value and the difference value.

16. The method of claim 15, wherein estimating the second blood pressure value comprises,
identifying an average blood pressure difference between blood pressure values of the first posture and blood pressure values of the second posture, included in the calibration data sets for the plurality of postures; and
when the average blood pressure difference is smaller than a first reference value, estimating the same value as the first blood pressure value as the second blood pressure value.

17. The method of claim 15, wherein estimating the second blood pressure value comprises,
when a difference between a first value obtained by applying the difference value to the first blood pressure value and a minimum blood pressure value included in the calibration data sets is a second reference value or more, identifying an average value of the first value and the minimum blood pressure value as the second blood pressure value.

18. The method of claim 14, wherein estimating the second blood pressure value comprises,
when a difference between a second value obtained by applying the difference value to the first blood pressure value and a maximum blood pressure value included in the calibration data sets is a second reference value or more, identifying an average value of the second value and the maximum blood pressure value as the second blood pressure value.

19. The method of claim 12, further comprising:
identifying the number of the plurality of calibration data sets; and
when the number of the plurality of calibration data sets is less than a specific number, displaying a message requesting to measure a blood pressure value for calibration in the second posture without performing the estimation of the second calibration information.

20. An electronic device comprising:
a memory;
a communication module; and
a processor,
wherein the processor is configured to,
obtain information about a user's first biometric signal measured in a user's first posture from a wearable electronic device, through the communication module,
obtain, from the external electronic device, information about the user's first blood pressure value measured by the external electronic device in the first posture, through the communication module,
obtain first calibration information for quantifying first blood pressure information measured in the first posture, based on information about features of the first biometric signal and the first blood pressure value,
identify whether calibration data sets for a plurality of postures of the user, pre-stored in the memory, meet a specific condition for estimating second calibration information for quantifying second blood pressure information measured in a user's second posture, and
when the calibration data sets meet the specific condition, estimate the second calibration information based on the calibration data sets and the first calibration information.

* * * * *